US008885905B2

(12) United States Patent
Dey et al.

(10) Patent No.: US 8,885,905 B2
(45) Date of Patent: Nov. 11, 2014

(54) METHOD AND SYSTEM FOR PLAQUE CHARACTERIZATION

(75) Inventors: Damini Dey, Los Angeles, CA (US); Piotr J. Slomka, Los Angeles, CA (US); Daniel S. Berman, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 225 days.

(21) Appl. No.: 13/513,842

(22) PCT Filed: Dec. 3, 2010

(86) PCT No.: PCT/US2010/058979
§ 371 (c)(1),
(2), (4) Date: Jun. 4, 2012

(87) PCT Pub. No.: WO2011/069120
PCT Pub. Date: Jun. 9, 2011

(65) Prior Publication Data
US 2012/0243764 A1    Sep. 27, 2012

Related U.S. Application Data

(60) Provisional application No. 61/266,441, filed on Dec. 3, 2009.

(51) Int. Cl.
| | |
|---|---|
| *G06K 9/00* | (2006.01) |
| *G06T 7/00* | (2006.01) |
| *A61B 6/00* | (2006.01) |
| *A61B 6/03* | (2006.01) |

(52) U.S. Cl.
CPC .............. *A61B 6/504* (2013.01); *G06T 7/0012* (2013.01); *G06T 2207/30048* (2013.01); *A61B 6/503* (2013.01); *G06T 2207/30172* (2013.01); *A61B 6/032* (2013.01); *G06T 2207/10081* (2013.01)
USPC .......................................... 382/131; 600/425

(58) Field of Classification Search
None
See application file for complete search history.

(56) References Cited

U.S. PATENT DOCUMENTS

| | | |
|---|---|---|
| 7,356,367 B2 | 4/2008 | Liang et al. |
| 7,558,611 B2 | 7/2009 | Arnold et al. |

(Continued)

FOREIGN PATENT DOCUMENTS

WO    WO2011069120    6/2011

OTHER PUBLICATIONS

IPRP for PCTUS2010058979.
ISR for PCTUS2010058979.
Written Opinion for PCTUS2010058979.

(Continued)

*Primary Examiner* — Bhavesh Mehta
*Assistant Examiner* — Siamak Harandi
(74) *Attorney, Agent, or Firm* — Hema Vakharia-Rao; Nixon Peabody LLP

(57) ABSTRACT

A method of quantifying plaques imaged by cardiac computed tomography angiography ("CCTA") scan data. Calcified and non-calcified component thresholds are determined based at least in part on attenuation values of a pool of blood in the CCTA scan data. An epicardial fat threshold is determined and used to classify epicardial fat in the CCTA scan data. A portion of CCTA scan data positioned between a detected outer boundary of the coronary artery and a portion classified as lumen is classified as arterial wall. NCP and CP seeds are identified in the arterial wall portion. Portions of the CCTA scan data continuous with a NCP seed and having attenuation values greater than an artery wall value and less than the NCP threshold are classified as NCP, and portions of the CCTA scan data continuous with the CP seed and having attenuation values greater than the CP threshold are classified as CP.

42 Claims, 12 Drawing Sheets

(56) References Cited

U.S. PATENT DOCUMENTS

| | | |
|---|---|---|
| 2003/0176780 A1* | 9/2003 | Arnold et al. ............... 600/407 |
| 2008/0103389 A1* | 5/2008 | Begelman et al. ........... 600/425 |
| 2008/0137926 A1* | 6/2008 | Skinner et al. .............. 382/131 |
| 2008/0187199 A1 | 8/2008 | Gulsun et al. |

OTHER PUBLICATIONS

Dey et al. "Automated 3-dimensional quantification of noncalcified and calcified coronary plaque from coronary CT angiography" Nov. 2009, Epub Oct. 1, 2009.

* cited by examiner

METHOD AND SYSTEM FOR PLAQUE CHARACTERIZATION

CROSS REFERENCE TO RELATED APPLICATION(S)

This application is the National Phase of International Application PCT/US10/58979, filed Dec. 3, 2010, which designated the U.S. and that International Application was published under PCT Article 21(2) in English. The present application also claims the benefit of the filing date of U.S. Provisional Application No. 61/266,441 filed Dec. 3, 2009 the disclosure of which is incorporated herein by reference in its entirety.

BACKGROUND OF THE INVENTION

1. Field of the Invention

The present invention is directed generally to methods of analyzing plaques formed in arterial walls of coronary arteries.

2. Description of the Related Art

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Each year, one million people in the United States and nineteen million people worldwide experience a sudden acute coronary event (sudden cardiac death or myocardial infarction). See Yusuf S., Reddy S., Ounpuu S., Anand S., Global burden of cardiovascular diseases: part I: general considerations, the epidemiologic transition, risk factors, and impact of urbanization, *Circulation*, 2001; 104(22):2746-53. Early detection and accurate assessment of coronary artery disease is crucial in the identification of patients at risk of these highly common yet usually preventable coronary events.

Although the current standard for assessing coronary artery disease is the identification of anatomically significant coronary luminal stenosis by invasive coronary angiography, it is known that most acute coronary syndromes arise from plaques that are not critically occlusive. See Falk E., Fuster V., Angina pectoris and disease progression, *Circulation*, 1995; 92(8):2033-5, and Virmani R., Burke A. P., Farb A., Kolodgie F. D., Pathology of the vulnerable plaque, *J. Am. Coll. Cardiol.*, 2006; 47 (8 Suppl):C13-8. Histopathologic analyses have shown that the "vulnerable" plaques considered responsible for acute coronary events have a large lipid pool, a thin cap, and macrophage-dense inflammation on or beneath their surfaces. See Virmani R., Kolodgie F. D., Burke A. P., Farb A., Schwartz S. M., Lessons from sudden coronary death: a comprehensive morphological classification scheme for atherosclerotic lesions, *Arterioscler Thromb Vasc Biol.*, 2000; 20(5):1262-75. This strongly suggests that plaque composition and structure may be associated with future coronary events. See Akram K., Rinehart S., Voros S., Coronary arterial atherosclerotic plaque imaging by contrast-enhanced computed tomography: Fantasy or reality?, *J. Nucl. Cardiol.*, 2008; 15(6):818-29, and Narula J., Finn A. V., Demaria A. N., Picking plaques that pop, *J. Am. Coil. Cardiol.*, 2005; 45(12): 1970-3. Therefore, a need exists for methods and systems that determine plaque composition.

Cardiac computed tomography angiography ("CCTA") is an imaging method that uses a computed tomography ("CT") scanner to image structures and blood vessels of the heart. CCTA performed using a 64-slice CT scanner has recently become an increasingly effective clinical tool for noninvasive assessment of the coronary arteries and for assessing plaque composition. See Achenbach S., Cardiac CT: state of the art for the detection of coronary arterial stenosis, *J. Cardiovasc. Comput. Tomogr.*, 2007; 1(1):3-20, and Berman D. S., Shaw L. J., Hachamovitch R., Friedman J. D., Dm Polk, Hayes S. W., Thomson L. E., Germano G., Wong N. D., Kang X., Rozanski A., Comparative use of radionuclide stress testing, coronary artery calcium scanning, and noninvasive coronary angiography for diagnostic and prognostic cardiac assessment, *Semin. Nucl. Med.*, 2007; 37(1):2-16. CCTA has also shown substantial potential for in vivo plaque component characterization. See Leber A. W., Becker A., Knez A., von Ziegler F., Sirol M., Nikolaou K., Ohnesorge B., Fayad Z. A., Becker C. R., Riser M., Steinbeck G., Boekstegers P., Accuracy of 64-slice computed tomography to classify and quantify plaque volumes in the proximal coronary system: a comparative study using intravascular ultrasound, *J. Am. Coll. Cardiol.*, 2006; 47(3):672-7; Leber A. W., Knez A., Becker A., Becker C., von Ziegler F., Nikolaou K., Rist C., Reiser M., White C., Steinbeck G., Boekstegers P., Accuracy of multidetector spiral computed tomography in identifying and differentiating the composition of coronary atherosclerotic plaques: a comparative study with intracoronary ultrasound, *J. Am. Coll. Cardiol.*, 2004; 43(7):1241-7; Leber A. W., Knez A., von Ziegler F., Becker A., Nikolaou K., Paul S., Wintersperger B., Reiser M., Becker C. R., Steinbeck G., Boekstegers P., Quantification of obstructive and nonobstructive coronary lesions by 64-slice computed tomography: a comparative study with quantitative coronary angiography and intravascular ultrasound, *J. Am. Coll Cardiol.*, 2005; 46(1): 147-54; and Petranovic M., Soni A., Bezzera H., Loureiro R., Sarwar A., Raffel C., Pomerantsev E., Jang I. K., Brady T. J., Achenbach S., Cury R. C., Assessment of nonstenotic coronary lesions by 64-slice multidetector computed tomography in comparison to intravascular ultrasound: evaluation of non-culprit coronary lesions, *J. Cardiovasc. Comput. Tomogr.*, 2009; 3(1):24-31.

A plaque may include non-calcified and/or calcified components. In CCTA scan data, attenuation thresholds may be used to identify structures, such as plaques, and evaluate their compositions. For example, the CCTA scan data may be used to determine whether a plaque contains non-calcified components and/or calcified components. Further, the CCTA scan data may be used to determine the percentage of a plaque this non-calcified versus calcified.

Unfortunately, plaque attenuation thresholds have been shown to vary significantly with intracoronary lumen attenuation and choice of reconstruction kernel. Therefore, plaque attenuation thresholds may vary between patients as well as between scans. In other words, plaque attenuation thresholds are patient and scan specific. See Cademartiri F., Mollet N. R., Runza G., Bruining N., Hamers R., Somers P., Knaapen M., Verheye S., Midiri M., Krestin G. P., de Feyter P. J., Influence of intracoronary attenuation on coronary plaque measurements using multislice computed tomography: observations in an ex vivo model of coronary computed tomography angiography, *Eur. Radiol.*, 2005; 15(7):1426-31; and Cademartiri F., La Grutta L., Runza G., Palumbo A., Maffei E., Mollet N. R., Bartolotta T. V., Somers P., Knaapen M., Verheye S., Midiri M., Hamers R., B ruining N: Influence of convolution filtering on coronary plaque attenuation values:

observations in an ex vivo model of multislice computed tomography coronary angiography, *Eur. Radiol.,* 2007; 17(7): 1842-9.

Currently, to evaluate plaques in CCTA scan data, the plaques must be identified manually and separated from other structures. In particular, accurate and reproducible measurement of coronary plaque has been limited by the need to manually trace contours separating epicardial fat from the vessel wall. Further, contours enclosing plaque components must also be manually traced. This manual tracing process is time consuming and can be prone to undesirable intra-observer variability. See Burgstahler C., Reimann A., Beck T., Kuettner A., Baumann D., Heuschmid M., Brodoefel H., Claussen C. D., Kopp A. F., Schroeder S., Influence of a lipid-lowering therapy on calcified and noncalcified coronary plaques monitored by multislice detector computed tomography: results of the New Age II Pilot Study, *Invest. Radiol.,* 2007; 42(3):189-95; and Schmid M., Achenbach S., Ropers D., Komatsu S., Ropers U., Daniel W. G., Pflederer T., Assessment of changes in non-calcified atherosclerotic plaque volume in the left main and left anterior descending coronary arteries over time by 64-slice computed tomography, *Am. J. Cardiol.,* 2008; 101(5):579-84.

Another approach used to evaluate plaque composition available in some current commercial implementations allows an operator to manually and interactively determine (or modify) the plaque attenuation thresholds used for each plaque. Like the other manual process mentioned above, establishing the plaque attenuation thresholds manually for each plaque may be time consuming and yield operator dependent results.

Standardized and automated quantification of non-calcified components, calcified components, and total plaque burden from CCTA scan data, although extremely challenging, is of great interest for refinement of cardiovascular risk stratification. See Akram K., Rinehart S., Voros S., Coronary arterial atherosclerotic plaque imaging by contrast-enhanced computed tomography: Fantasy or reality?, *J. Nucl. Cardiol.,* 2008; 15(6):818-29; and Schuijf J. D., Bax J. J., How do you quantify noncalcified plaque?, *J. Cardiovasc. Comput. Tomogr.,* 2008; 2(6):360-5. Although others have developed various methods for quantifying non-calcified plaque imaged by CCTA. See Clouse M. E., Sabir A., Yam C.-S., Yoshimura N., Lin S., Welty F., Martinez-Clark P., Raptopoulos V., Measuring noncalcified coronary atherosclerotic plaque using voxel analysis with MDCT angiography: a pilot clinical study, *AJR Am. J. Roentgenol.,* 2008; 190:1553-60.

Nevertheless, currently available technologies fail to provide a method or system capable of providing standardized and automated quantification of non-calcified and calcified components in clinical CCTA scan data captured by standard multi-slice CCTA scanners. Furthermore, currently available technologies also fail to provide a method or system capable of performing automated CCTA plaque segmentation, a key step toward standardized quantification of non-calcified and calcified components in plaques.

As an example, Clouse et al. supra, describes a "voxel analysis" technique that uses Analyze-Direct software (www.analyzedirect.com; Mayo Clinic, Rochester, Minn.). In this technique, expert readers manually draw eight perpendicular line profiles through a plaque, and attenuation values in eight radial voxels for each line profile are measured. Using these manually defined points, attenuation thresholds for the lumen, epicardial fat, and arterial wall are calculated from interpolation of the line profiles. Then, the lumen and plaque volumes are calculated.

Gertz et al. infra describe using 2D isotropic wavelet analysis to characterize micro-CT images of excised human coronary arteries. Compared with histology, they found that wavelet analysis allowed identification of coronary plaque components with 81% sensitivity and 86% specificity. See Gertz S. D., Bodmann B. G., Vela D., Papadakis M., Aboshady I., Cherukuri P., Alexander S., Kouri D. J., Baid S., Gittens A. A., Gladish G. W., Conyers J. L., Cody D. D., Gavish L., Mazraeshahi R. M., Wilner W. T., Frazier L., Madjid M., Zarrabi A., Lukovenkov S., Ahmed A., Willerson J. T., Casscells S. W., Three-dimensional isotropic wavelets for postacquisitional extraction of latent images of atherosclerotic plaque components from micro-computed tomography of human coronary arteries, *Acad. Radiol.,* 2007; 14(12): 1509-19.

Recent in vivo studies comparing manual plaque characterization from 64-slice CCTA to an invasive intravascular standard have found significant overlap between lipid-rich and fibrous non-calcified components and high intra-observer variability. See Leber 2006 supra; and Petranovic et al. supra.

Therefore, as explained above, a need exists for methods and systems capable of performing automated quantification of non-calcified and calcified components of plaques imaged in CCTA scan data. A method or system that provides standardize quantification of these components would be particularly desirable. The present application provides these and other advantages as will be apparent from the following detailed description and accompanying figures.

SUMMARY OF INVENTION

Aspects of the present application describe a computer implemented method that includes obtaining cardiac computed tomography angiography ("CCTA") scan data imaging a pool of blood, and a coronary artery having a lumen defined by an artery wall at least partially surrounded by epicardial fat. The CCTA scan data includes a plurality of attenuation values. A plurality of voxels may be associated with the plurality of attenuation values. An identification of a first portion of the plurality of attenuation values located within the pool of blood is received. Calcified and non-calcified component thresholds are each determined based at least in part on the first portion of the plurality of attenuation values. Identifications of a plurality of points positioned within the lumen of the coronary artery are received and one or more lines are generated from the plurality of points. The one or more lines may be curved (e.g., splines) and characterized as being centerlines. A vessel neighborhood is determined based on the one or more centerlines and a series of short-axis cross-sections through the coronary artery generated based on the one or more lines. Each of the short-axis cross-sections includes a point positioned on one of the one or more centerlines. Then, at least one epicardial fat region is identified within the vessel neighborhood of each of the series of short-axis cross-sections. An epicardial fat threshold ("EFT") value is determined based on ones of the plurality of attenuation values within the epicardial fat regions identified within each of the series of short-axis cross-sections. Portions of the series of short-axis cross-sections having attenuation values below the EFT value are classified as epicardial fat. The method classifies as lumen a connected portion of CCTA scan data adjacent the one or more centerlines and having attenuation values greater than the non-calcified component threshold and less than the calcified component threshold.

The method detects an outer boundary of the coronary artery within each of the series of short-axis cross-sections, and classifies as arterial wall a portion of CCTA scan data positioned between the outer boundary of the coronary artery and the portion classified as lumen. The outer boundary of the coronary artery may be detected by detecting, relative to the point positioned on one of the one or more lines, an outermost and maximum radial gradient boundary. The method may search for the outermost and maximum radial gradient boundary within portions of the CCTA scan data having attenuation values greater than the EFT value but significantly less than the non-calcified component threshold value.

An artery wall value is determined as a function of the ones of the attenuation values located within the portion of the CCTA scan data classified as arterial wall. The artery wall value may be an average of ones of the attenuation values located within the portion of the CCTA scan data classified as arterial wall.

At least one of a non-calcified component seed element and a calcified component seed element are identified in the portion classified as arterial wall. For each non-calcified component seed element identified, the method classifies as non-calcified components any portions of the CCTA scan data continuous with the non-calcified component seed element and having attenuation values that are greater than the artery wall value and less than the non-calcified component threshold value. For each calcified component seed element identified, the method classifies as calcified components any portions of the CCTA scan data continuous with the calcified component seed element and having attenuation values that are greater than the calcified component threshold value.

The method may include displaying at least a portion of the CCTA scan data with an overlay identifying one or more portions of the CCTA scan data classified as calcified components and one or more portions of the CCTA scan data classified as non-calcified components. Further, the method may include determining a non-calcified plaque volume for at least one portion of the CCTA scan data classified as non-calcified components, and/or determining a calcified plaque volume for at least one portion of the CCTA scan data classified as calcified components.

The method may include for each of the series of short-axis cross-sections, identifying attenuation values within the lumen of the coronary artery, and determining a normal contrast value based on the attenuation values identified as being within the lumen of the coronary artery. Then, a lower contrast level may be determined based on the first portion of the plurality of attenuation values. In such embodiments, the non-calcified component threshold may be determined as a function of the lower contrast level and the normal contrast value of a selected one of the series of short-axis cross-sections.

The selected one of the series of short-axis cross-sections may be selected based on whether the lumen of the coronary artery is completely occluded. Thus, the method may include determining whether the lumen of the coronary artery is completely occluded. If it is determined that the lumen of the coronary artery is completely occluded, a distal one of the series of short-axis cross-sections is selected as the selected one of the series of short-axis cross-sections. On the other hand, if it is determined that the lumen of the coronary artery is not completely occluded, a middle one of the series of short-axis cross-sections is selected as the selected one of the series of short-axis cross-sections.

Within each of the series of short-axis cross-sections, the normal contrast value may be determined by identifying a minimum attenuation value within the first portion of the plurality of attenuation values. Next, a region is grown from the point positioned on one of the one or more lines to include any portions of the CCTA scan data contiguous with the point and having attenuation values greater than the minimum attenuation value and less than the non-calcified component threshold value. Then, the normal contrast value is determined as a function of the attenuation values within the region grown from the point positioned on one of the one or more centerlines.

The calcified component threshold may be greater than a mean of the first portion of the plurality of attenuation values. In particular embodiments, the calcified component threshold is equal to a sum of a standard deviation of the first portion of the plurality of attenuation values multiplied by a value greater than one (e.g., 1.5, 2, 2.5, 3, etc.) and the mean of the first portion of the plurality of attenuation values.

The non-calcified component threshold may be less than a mean of the first portion of the plurality of attenuation values. In particular embodiments, the non-calcified component threshold is equal to a standard deviation of the first portion of the plurality of attenuation values multiplied by a value greater than one (e.g., 1.5, 2, 2.5, 3, etc.) and subtracted from the mean of the first portion of the plurality of attenuation values.

Aspects of the present application also describe one or more computer-readable media including instructions executable by one or more processors and when executed by the one or more processors causing the one or more processors to perform at least one of the methods described above.

Additional aspects of the present application also describe systems configured to perform at least one of the methods described above.

BRIEF DESCRIPTION OF THE SEVERAL VIEWS OF THE DRAWING(S)

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N. Y. 1994); March, Advanced Organic Chemistry Reactions, Mechanisms and Structure 4th ed., J. Wiley & Sons (New York, N. Y. 1992); and Sambrook and Russell, Molecular Cloning: A Laboratory Manual 3rd ed., Cold Spring Harbor Laboratory Press (Cold Spring Harbor, N. Y. 2001), provide one skilled in the art with a general guide to many of the terms used in the present application.

One skilled in the art will recognize many methods or materials similar or equivalent to those described herein, which could be used in the practice of the present invention. Indeed, the present invention is in no way limited to the methods or materials described.

Figure 1:
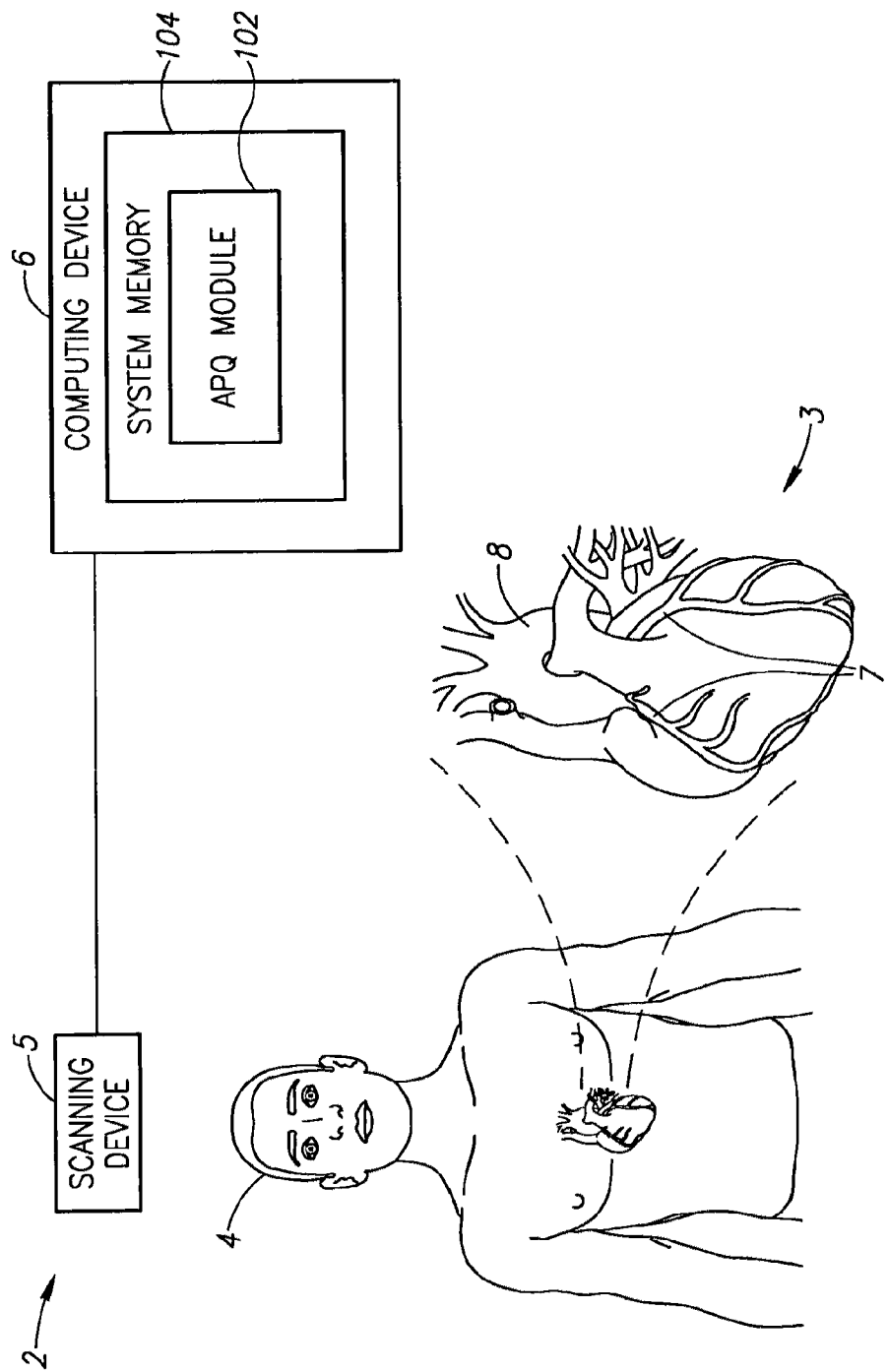
FIG. 1 is a block diagram of a system for analyzing plaques formed in an arterial wall of a coronary artery of a heart of a patient.

FIG. 1 is a block diagram of a system 2 for creating and analyzing CCTA scans of a heart 3 of a patient 4. The system 2 includes a scanning device 5 configured to perform CCTA scans of the patient's heart 3 to obtain CCTA scan data. The CCTA scan data is analyzed by a computing device 6 connected to the scanning device 5.

As is apparent to those of ordinary skill in the art, the scanning device 5 captures X-ray attenuation values that may be used to construct a 2D representation of the patient's heart 3, or a portion thereof. The attenuation values (e.g., measured in Hounsfield units ("HU")) each indicate an amount by which X-rays are attenuated (e.g., scattered or absorbed) by the heart 3 in a particular location. The attenuation values may be mapped to grayscale levels (or colors) and displayed to an operator. Further, a contrast agent may be injected into the blood stream and used to enhance attenuation.

The scanning device 5 captures multiple images of the heart 3 from outside the chest. Generally, transaxial images are captured along a longitudinal (or long) axis of the body. The three dimensional representation is typically constructed (e.g., by the computing device 6) from a plurality or stack of transaxial images.

As is apparent to those of ordinary skill in the art, the patient's heart 3 includes coronary arteries 7 that are connected to an aorta 8. The three dimensional representation of the coronary arteries 7 or the aorta 8 may be rotated and position so that longitudinal cross-sections of the coronary artery may be displayed. Further, ring-shaped short-axis cross-sections of the coronary arteries 7 or the aorta 8 may be generated that are perpendicular to the longitudinal cross-sections.

Figure 2:
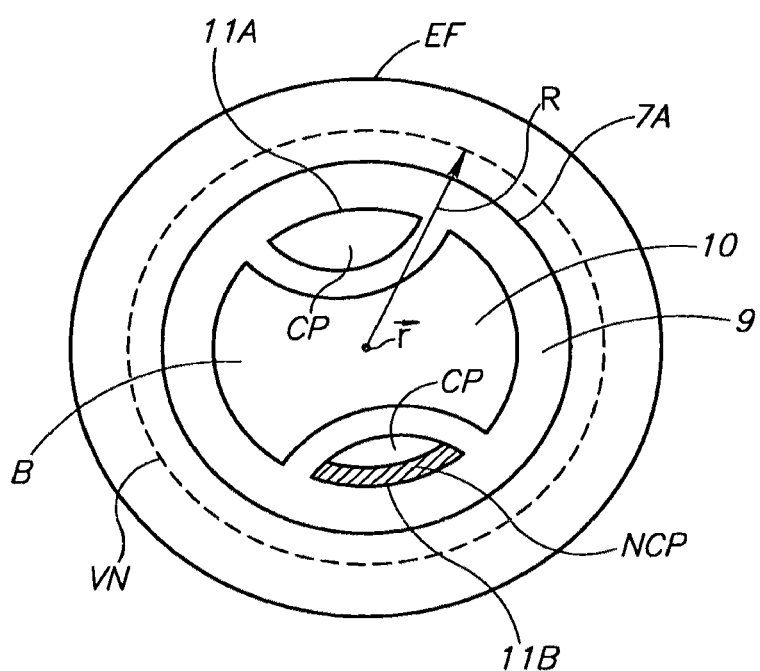
FIG. 2 is a short-axis cross-section of a coronary artery illustrating a first and second plaque.
Figure 3:
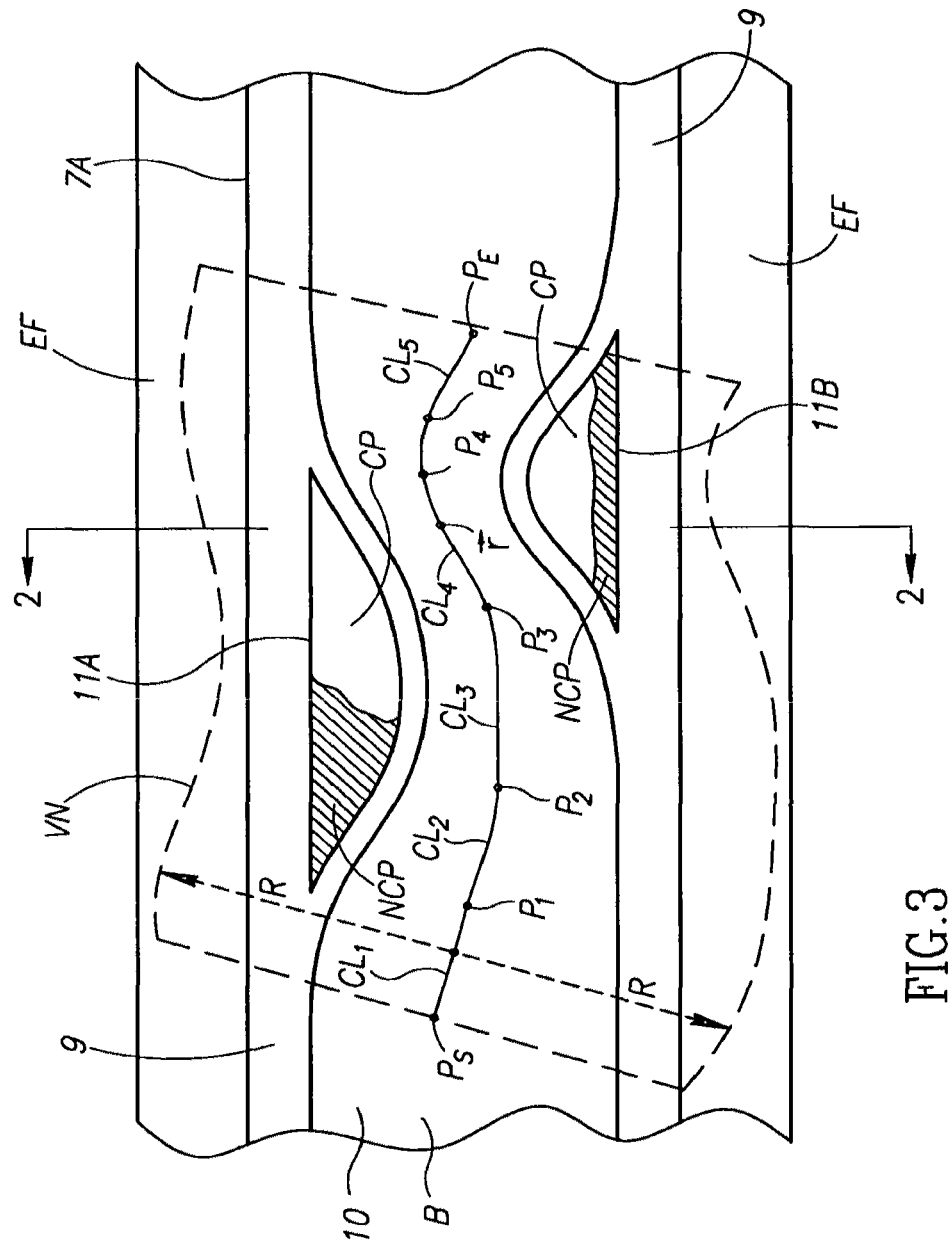
FIG. 3 is a longitudinal cross-section of the coronary artery illustrated in FIG. 2.

FIG. 2 is an illustration of a short-axis cross-section of an exemplary coronary artery 7A and FIG. 3 is a longitudinal cross-section of the coronary artery 7A. As may be seen in FIGS. 2 and 3, the coronary artery 7A is at least partially surrounded by epicardial fat "EF." The coronary artery 7A includes an arterial wall 9 defining a lumen 10. Blood "B" flows through unobstructed portions of the lumen 10.

One or more plaques (e.g., plaques 11A and 11B) may form inside the arterial wall 9. Each of the plaques 11A and 11B may be calcified, non-calcified, or a combination thereof. The plaques 11A and 11B narrow the lumen 10 and at least partially obstruct the flow of blood "B" therethrough. For ease of illustration, each of the plaques 11A and 11B is illustrated as including non-calcified components "NCP" and calcified components "CP."

Petranovic et al. supra reported mean attenuation values of about 275.3+/−77.2 HU for coronary lumen, about 117.9+/−94.2 HU for non-calcified components, and about 608.2+/−216.9 HU for calcified components, with the mean attenuation values for non-calcified and calcified components differing significantly from one another. While this suggests accurate quantification of non-calcified and calcified components may be possible using CCTA scan data, the data also shows that the lower threshold value of 130 HU (used extensively for calcified component quantification from non-contrast CT) cannot be applied for calcified component quantification from CCTA scan data without also including significant non-calcified components. See Petranovic et al. supra.; Agatston A. S., Janowitz W. R., Hildner F. J., Zusmer N. R., Viamonte M. Jr., Detrano R., Quantification of coronary artery calcium using ultrafast computed tomography, *J. Am. Coll. Cardiol.*, 1990; 15(4):827-32; and Callister T., Cooil B., Raya S., Lippolis N., Russo D., Raggi P., Coronary artery disease: improved reproducibility of calcium scoring with an electron-beam CT volumetric method, Radiology, 1998; 208(3):807-14.

Previous studies have described contrast enhancement of atherosclerotic plaque with the use of human coronary artery specimens. See Cademartiri et al. (2005) supra; and Halliburton S. S., Schoenhagen P., Nair A., Stillman A., Lieber M., Murat Tuzcu E, Geoffrey Vince D, White RD: Contrast enhancement of coronary atherosclerotic plaque: a high-resolution, multidetector-row computed tomography study of pressure-perfused, human ex-vivo coronary arteries, *Coron. Artery. Dis.*, 2006; 17(6):553-60. By using multi-slice CT, intravascular ultrasound ("IVUS") scanning, and histology, Halliburton et al. supra demonstrated that intra-arterial injection of iodinated contrast agent results in the enhancement of arterial lumen as well as significant enhancement of atherosclerotic plaque.

While the use of contrast may enhance various structures (e.g., the lumen and plaques), the use of contrast alone does not adequately distinguish the attenuation values to allow for a simple determination of attenuation threshold values for the non-calcified and calcified components of the plaques. For example, Cademartiri et al. (2005) supra scanned ex vivo specimens of human coronary arteries injected with four different dilutions of contrast material with multi-slice CT and determined the attenuation values observed in the lumen and plaque was significantly different for each dilution of contrast material. Cademartiri et al. (2005) supra also concluded that plaque attenuation varies with intracoronary attenuation and recommended that luminal attenuation be taken into account for plaque characterization. Cademartiri et al. (2007) supra further demonstrated that plaque attenuation varies significantly with the choice of reconstruction kernel.

Figure 4:
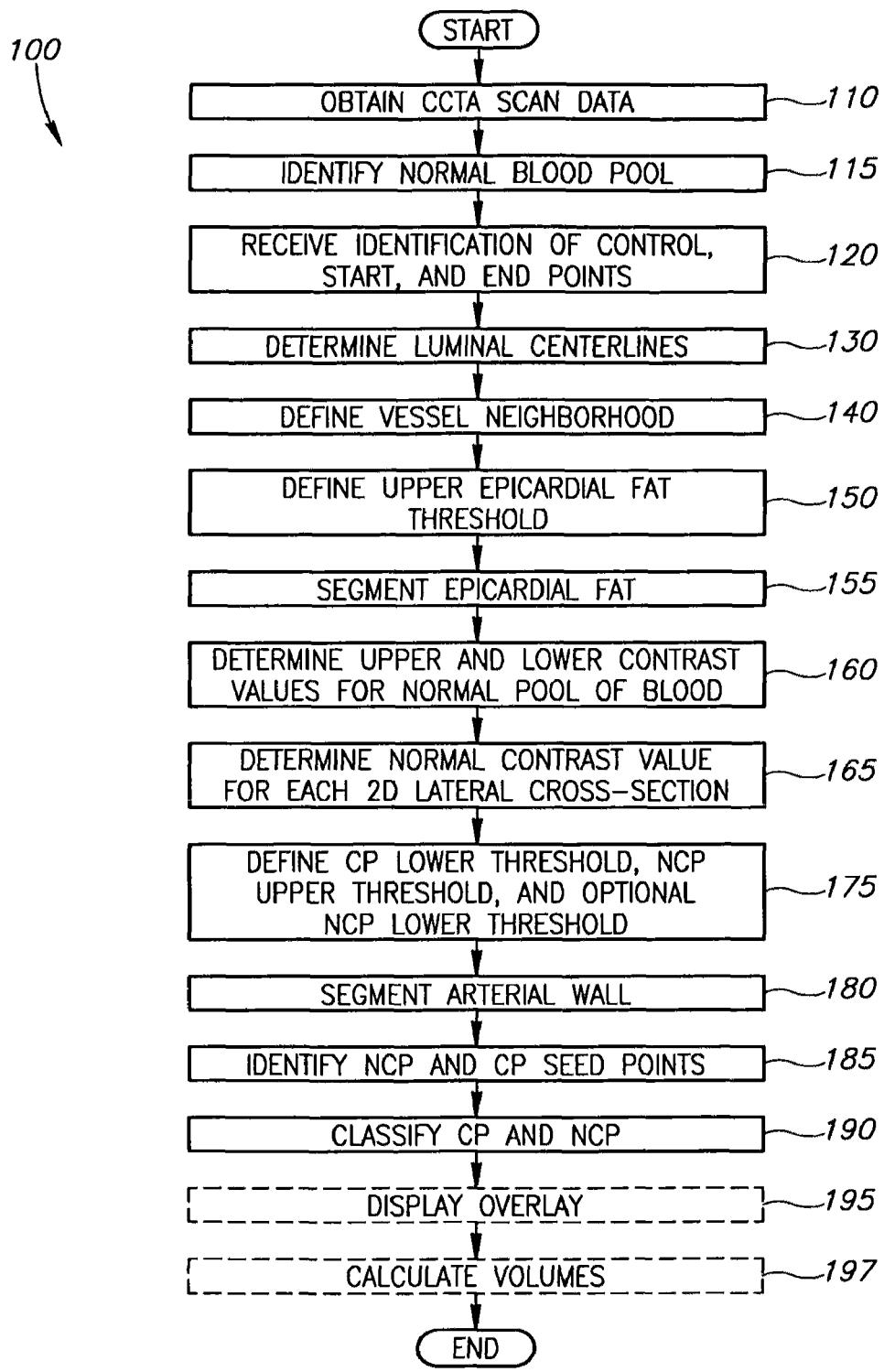
FIG. 4 is a flow diagram of a method of segmenting and quantifying non-calcified and calcified components of plaques.

FIG. 4 is a flow diagram of a method 100 that may be performed by the system 2 (see FIG. 1) to segment and quantify the non-calcified and calcified components "NCP" and "CP" of the plaques 11A and 11B illustrated in FIGS. 2 and 3. The method 100 is described below with respect to FIGS. 1-4.

Portions of the method 100 may be performed by the computing device 6 (see FIG. 1) executing an automated computer algorithm implemented by an APQ module 102. A hardware and an operating environment in conjunction with which implementations of the computing device 6 may be practiced is described in detail below with respect to FIG. 10. In addition to other components described below, the computing device 6 includes a system memory 104 in which the APQ module 102 may be stored.

The APQ module 102 quantifies the plaques 11A and 11B in three dimensions. However, two-dimensional ("2D") short-axis and/or longitudinal cross-sections of the coronary artery 7A are considered in several blocks of the method 100. Optionally, a portion of these 2D cross-sections may be displayed as 2D cross-sectional images. However, this is not always necessary. In particular, when automatic operations are performed on such 2D cross-sections, they need not be displayed.

When executed by one or more processors (e.g., a processing unit 21 illustrated in FIG. 10), the APQ module 102 causes the one or more processors to derive scan-specific attenuation thresholds for the lumen 10 (or blood "B" therein), the non-calcified coronary plaque components "NCP," the calcified coronary plaque components "CP," and epicardial fat "EF" from individual CCTA scans. These threshold values may be used to segment the lumen 10, the non-calcified coronary plaque components "NCP," the calcified coronary plaque components "CP," and epicardial fat "EF" within the CCTA scan data.

The APQ module 102 may be configured (when executed) to perform knowledge-based segmentation of coronary arteries and geometrical coronary artery modeling. When executed, the APQ module 102 may also be configured to perform connected voxel grouping in three dimensions to quantify the non-calcified and calcified coronary plaque components "NCP" and "CP" of the plaques 11A and 11B. By way of a non-limiting example, the APQ module 102 may be configured to determine volumes of the non-calcified and calcified components "NCP" and "CP" of the plaques 11A and 11B. Depending upon the implementation details, plaque quantification results obtained by the method 100 may be highly reproducible, and obtained in a fraction of the time (2%) needed to perform a manual analysis.

As is apparent to those of ordinary skill in the art, the plaques 11A and 11B are located within the arterial wall 9. Therefore, to identify the non-calcified and calcified components "NCP" and "CP" of the plaques 11A and 11B, segmentation of the arterial wall 9 from other structures, such as the blood "B" and the epicardial fat "EF" is necessary. As will be described below, to perform this segmentation, the method 100 determines scan-specific attenuation thresholds for the non-calcified and calcified components "NCP" and "CP" of the plaques 11A and 11B based at least in part on luminal attenuation values.

An implementation of the method 100 was initially tested visually and later refined using a separate training group of 35 CCTA datasets acquired previously as described in Dey D., Lee C. J., Ohba M., Gutstein A., Slomka P. J., Cheng V., Suzuki Y., Suzuki S., Wolak A., Le Meunier L., Thomson L. E. J., Cohen I., Friedman J. F., Germano G., Berman D. S., Image quality and artifacts in coronary CT angiography with dual-source CT: initial clinical experience, *J. Cardiovasc. Comput. Tomogr.*, 2008; 2:105-14; and Cheng V., Nakazato R., Dey D., Gurudevan S., Tabak J., Budoff M. J., Karlsberg R. P., Min J., Berman D. S., Reproducibility of coronary artery plaque volume and composition quantification by 64-detector row coronary computed tomographic angiography: an intraobserver, interobserver, and interscan variability study [published online ahead of print Jul. 31, 2009], *J. Cardiovasc. Comput. Tomogr.*, doi: 10.1016/j.jcct.2009.07.001.

In first block 110, the scanner device 5 captures conventional multi-slice CCTA scan data (also referred to herein as a CCTA dataset) for the patient 4. Methods of performing conventional multi-slice CCTA scans are known in the art and will not be described in detail.

Then, the CCTA scan data captured in block 110 is accessible by (e.g., transferred to) the computing device 6.

In block 115, the computing device 6 displays a (3D or 2D) representation of the CCTA scan data to an operator who identifies one or more regions of interest in the center (i.e., within a lumen) of the aorta 8. As discussed above, the computing device 6 may display cross-sections along the short-axis and/or longitudinal axis of an artery (e.g., the coronary artery 7A, the aorta 8, and the like). By way of a non-limiting example, in block 115, the operator may identify a region of interest (within the lumen of the aorta 8) in transaxial images of the aortic root. The one or more regions of interest are used to define a "normal blood pool" from which attenuation values for blood may be obtained. By way of an example, a single region of interest may be used to define the "normal blood pool." Thus, in block 115, the computing device 6 receives input (namely, the identification of one or more regions of interest) from the operator.

Next, the operator turns his/her attention to a coronary artery (e.g., the left anterior descending coronary artery) of interest. For ease of illustration, the coronary artery 7A depicted in FIGS. 2 and 3 will be described as being the coronary artery of interest. However, the coronary artery of interest may be any coronary artery and the method 100 is not limited to use with any particular coronary artery.

In block 120, the computing device 6 displays a (3D or 2D) representation of the CCTA scan data to the operator. Within the representation displayed to the operator, the operator locates the coronary artery 7A and identifies a plurality of control points (e.g., control points "$P_1$"-"$P_5$"), a start point "$P_S$," and an end point "$P_E$" within a portion of the coronary artery 7A. By way of a non-limiting example, the control points "$P_1$"-"$P_5$," the start point "$P_S$," and/or the end point "$P_E$" may be defined in 3D using both short-axis and longitudinal cross-sections of the coronary artery 7A. Thus, in block 120, the computing device 6 receives input from the operator. For ease of illustration, in block 120, the start and end points "$P_S$" and "$P_E$" flank a portion of the coronary artery 7A that includes the plaques 11A and 11B.

By way of a non-limiting example, the operator may specify five to seven control points. The control points "$P_1$"-"$P_5$" are each positioned in the arterial lumen 10 of the coronary artery 7A adjacent to but spaced apart from the plaques 11A and 11B (which are located between the start and end points "$P_S$" and "$P_E$"). By way of a non-limiting example, the operator may specify a control point in each of a plurality of 2D short-axis cross-sectional images. Alternatively, as illustrated in FIG. 3, the operator may specify multiple control points in a 2D longitudinal cross-section. By way of yet another example, the operator may specify the control points in a 2D representation of the coronary artery 7A.

In block 130, the computing device 6 automatically determines one or more luminal centerlines (e.g., centerlines "$CL_1$"-"$CL_6$") using the control points "$P_1$"-"$P_5$," the start point "$P_S$," and the end point "$P_E$." Generally, the luminal centerlines "$CL_1$"-"$CL_6$" will be positioned within the blood flow in the arterial lumen 10. Multiple luminal centerlines may be connected together to define a continuous pathway through the arterial lumen 10. By way of a non-limiting example, the luminal centerlines "$CL_1$"-"$CL_6$" may be determined by fitting a piecewise cubic Catmull-Rom spline function to the control points "$P_1$"-"$P_5$," the start point "$P_S$," and the end point "$P_E$." See Catmull E., and Rom R., A class of local interpolating splines, *Proc. Int. Conf. Comput. Aided. Geom. Des.*, 1974; 74:317-26.

As mentioned above, the plaques 11A and 11B are located within the arterial wall 9. Therefore, the arterial lumen 10 (and blood "B" therein) may be removed or segmented from the arterial wall 9 when the plaques 11A and 11B are analyzed. To reduce the likelihood of bias caused by incorrect arterial lumen segmentation, in block 140, the computing device 6 may automatically define a vessel neighborhood "VN" along the luminal centerlines "$CL_1$"-"$CL_6$," having a maximum radius "R" from the luminal centerlines. Because coronary artery diameter is typically less than or equal to about 3 mm (see Achenbach S., Computed tomography coronary angiography, *J. Am. Coll. Cardiol.*, 2006; 48(10):1919-28), a slightly higher value (e.g., 4 mm) may be used to make sure the entire portion of the coronary artery 7A between the start and end points "$P_S$" and "$P_E$" is considered when the lumen 10 is segmented. By way of a non-limiting example, the maximum radius "R" may be about 2.0 mm.

In block 150, the computing device 6 determines a scan-specific epicardial fat threshold ("EFT") value for the coronary artery 7A. For example, in block 150, using geometry, the computing device 6 may define a 3D-2D correspondence for the vessel neighborhood "VN." By way of a non-limiting example, the 3D-2D correspondence for the vessel neighborhood "VN" may be defined using Eq. #1 and Eq. #2 as follows.

Given successive points "$\not{p}$" and "$\not{q}$" (e.g., a pair of successive points between the control points "$P_3$" and "$P_4$") along a centerline (e.g., the control points "$CL_4$"), an interpolated point "$\not{r}$" may be computed as a convex combination in accordance with equation ("Eq.") #1.

$$\not{r} = \not{p} + (1-\gamma)\not{q}, 0 \leq \gamma \leq 1 \qquad \text{(Eq. #1)}$$

A 2D short-axis cross-section, perpendicular to the direction of vector ($\not{p} - \not{q}$), is then created with the interpolated point "$\not{r}$" as a center, and basis vectors "$\hat{a}$" and "$\hat{b}$" that span the 2D short-axis cross-section. Every point "$\not{r}$" on the 2D short-axis cross-section can be represented by polar representation ($\rho$, $\theta$):

$$\not{r} = \not{r} + \rho \cos(\theta) \cdot \hat{a} + \rho \sin(\theta) \cdot \hat{b}, 0 \leq \rho \leq R, 0 \leq \theta \leq 2\pi \qquad \text{(Eq. #2)}$$

In Eq. #2, the variable "R" is the maximum radius "R" used to define the vessel neighborhood "VN." A step size may be used to define the 2D short-axis cross-sections.

FIG. 2 depicts the 2D short-axis cross-section having the interpolated point "$\not{r}$" as its center. To calculate the EFT value for the vessel neighborhood "VN" in a 2D short-axis cross-section (e.g., the 2D short-axis cross-section depicted in FIG. 2), the computing device 6 searches radially inwardly, toward the luminal centerline (e.g., toward the interpolated point "$\not{r}$"). An initial (or preset) EF threshold value may be used to identify the epicardial fat "EF" in the 2D short-axis cross-section. For example, the initial EF threshold value may be −10 HU, which is a value obtained by manual measurement from the CCTA datasets in the training group described above with respect to block 110. Regions of the 2D short-axis cross-section having attenuation values less than the initial EF threshold value may include the epicardial fat "EF."

Next, an epicardial fat area is identified. The epicardial fat area may be identified using fat thresholds to define an epicardial fat range of attenuation values. By way of a non-limiting example, it is well-validate that epicardial fat may have attenuation values of about −30 HU to about −190 HU. The initial EF threshold may simply serve as an upper limit. In other words, the epicardial fat area may include any portions of the CCTA scan data having attenuation values less than the initial EF threshold.

Then, the (upper) EFT value is determined based on attenuation values within the epicardial fat area. For example, a mean attenuation ("m") value and standard deviation ("SD") value may be calculated for the epicardial fat area and the EFT value determined based on the mean attenuation ("m") value and standard deviation ("SD") values. By way of a non-limiting example, the EFT value may be defined using the Eq. #3, in which the ETF value is equal to a sum of the mean attenuation ("m") and three times the standard deviation ("SD"):

$$EFT = m + 3SD \qquad \text{(Eq. #3)}$$

This relationship gave the best agreement with manual measurement from the sample group.

Then, in block 155, the EFT value is used to segment a region believed to include the epicardial fat "EF." For example, any region having attenuation values less than the EFT value may be classified as being epicardial fat. Then, the regions classified as epicardial fat may be segmented from the remainder of the CCTA scan data.

In block 160, the computing device 6 determines a range of attenuation (or contrast) values for the normal blood pool. By way of a non-limiting example, in block 160, the normal blood pool region in the aorta 8 (identified in block 115) may be filtered with a median filter, and an image histogram computed. Then, a Gaussian curve may be fitted to the smoothed image histogram (e.g., using an iterative Levenberg-Marquardt algorithm). See Dey D., Callister T. Q., Slomka P. J., Aboul-Enein F., Nishina H., Kang X., Gransar H., Wong N. D., Miranda-Peats R., Hayes S., Friedman J. D., Berman D. S., Computer-aided detection and evaluation of lipid-rich plaque in non-contrast cardiac computed tomography, *AJR Am J. Roentgenol.*, 2006; 186(6 Suppl. 2):S407-13; and *Numerical recipes in C the art of scientific computing [computer program]*, Version 2nd, Acrobat. Cambridge, N.Y.: Cambridge University Press; 2000.

A peak value ("p") corresponding to normal contrast (or the attenuation of the blood) in the aorta 8, as well as a standard deviation ("σ"), may be obtained from the fitted Gaussian curve. A lower contrast level ("l") and an upper contrast level ("u") may be defined in accordance with Eq. #4L and Eq. #4U, respectively. See Raggi P., Callister T. Q., Cooil B., Calcium scoring of the coronary artery by electron beam CT: how to apply an individual attenuation threshold, *AJR Am J. Roentgenol.*, 2002; 178(2):497-502.

$$l = p - 3\sigma \quad \text{(Eq. #4L)}$$

$$u = p + 3\sigma \quad \text{(Eq. #4U)}$$

Thus, at this point, the lower contrast level ("l") and upper contrast level ("u") for blood have been determined and may be used to segment blood (or the lumen 10) from the coronary artery 7A. A minimum normal blood pool contrast (or attenuation) value observed within the normal blood pool may also be stored for later use.

Next, in block 165, a normal contrast value is determined for each 2D short-axis cross-section. The normal contrast value may be calculated using 2D region growing. The region growing may start from the interpolated luminal centerline point "$\not{p}$" defined by Eq. #1, which is likely to be located in the blood flow. The region is grown from the interpolated point "$\not{p}$" to include points having a contrast value greater than an initial lower contrast threshold (e.g., the minimum normal blood pool contrast value) and below the upper contrast level ("u") determined by Eq. #4U. Thus, in block 165, within each 2D short-axis cross-section, a region likely to contain only blood is identified. The normal contrast value for the 2D short-axis cross-section may be set to an average normal contrast value within the region.

Optionally, for each 2D short-axis cross-section, a contrast distribution factor ("CDF") is defined. By way of a non-limiting example, the CDF may be defined in accordance with Eq. #5.

$$CDF = C_i / C_{i-1} \quad \text{Eq. #5}$$

In Eq. #5, $C_i$ is the average normal contrast computed for the 2D short-axis cross-section "i," and "i−1" is the average normal contrast computed for a previous, more proximal 2D short-axis cross-section. Thus, the CDF is a ratio of change from a more proximal 2D short-axis cross-section "i−1" to the current 2D short-axis cross-section "i."

Next, in block 175, the computing device 6 determines an NCP upper threshold (which may be stored in a variable "nt"), and a CP lower threshold based at least in part on luminal attenuation values observed in the lumen of the aorta 8 (and determined in blocks 160-165). Algorithms similar to those developed for non-contrast cardiac CT and described in Dey, et al. (2006) supra may be used to calculate these scan-specific thresholds. Optionally, the computing device 6 may determine an NCP lower threshold.

In block 175, the NCP upper threshold is defined (as a corrected lower contrast threshold) by multiplying lower contrast level ("l") by the normal contrast value of a selected 2D short-axis cross-section. If the plaques 11A and 11B are not completely occluding the coronary artery 7A, the normal contrast value of the middle 2D short-axis cross-section may be used. On the other hand, in the case of total occlusion, the normal contrast value of the most distal 2D short-axis cross-section may be used. Thus, within the CCTA scan data, regions having attenuation values less than the NCP upper threshold (which is the lower contrast level ("l") multiplied by the selected CDF) may contain the non-calcified components "NCP" of the plaques 11A and 11B. The optional NCP lower threshold may be set equal to the EFT value. Thus, regions having an attenuation value between the EFT and the NCP upper threshold may contain the non-calcified components "NCP" of the plaques 11A and 11B.

The CP lower threshold is set to the upper contrast level ("u") as defined in Eq. #4U. Thus, within the CCTA scan data, regions having attenuation values greater than the upper contrast level ("u") may contain the calcified components "CP" of the plaques 11A and 11B.

Further, within the CCTA scan data, regions having attenuation values less than the CP lower threshold and greater than the NCP upper threshold may contain the blood "B" within the lumen 10. Thus, such regions may be classified as being blood or lumen and segmented.

The upper contrast level ("u"), the lower contrast level ("l") the NCP upper threshold, and the CP lower threshold were tested by varying the constant (e.g., three) by which the standard deviation is multiplied as well as by using the full-width tenth maximum. Such tests revealed that multiplying the standard deviation by three yielded visually the best results in the training group, and was subsequently used in a study (described below).

In block 180, the computing device 6 segments the arterial wall 9. Although coronary plaques are easily visualized using CCTA scan data, it is known that visualization of the coronary arterial wall 9 (which has a typical thickness of about 1 mm) is challenging because of partial volume effects. See Akram, et al., supra. To segment the arterial wall 9, the computing device 6 may use a multistep adaptive algorithm. Using this approach, the vessel neighborhood "VN" is refined using 2D region growing from the interpolated luminal centerline points (e.g., the interpolated point "$\not{p}$" defined by Eq. #1), using the EFT value as a lower threshold. This redefined vessel neighborhood may include voxels representing both (a) the arterial wall 9 and (b) volume-averaged wall and epicardial fat "EF."

In other words, the redefined vessel neighborhood includes the arterial wall 9 and an outmost portion of the arterial wall combined with epicardial fat "EF" by the process that constructed the 3D representation of the coronary artery 7A. This outer portion will have a generally lower attenuation value (because of the contribution of the epicardial fat "EF") than the other portions of the arterial wall. Optionally, the redefined vessel neighborhood may include the region(s) classified as blood (or lumen). Alternatively, these regions may be excluded from the redefined vessel neighborhood.

Thus, a radial change in attenuation may be used to identify the lower attenuation outer region including volume-averaged wall and epicardial fat "EF." In particular, one or more edge detection operations may be used to identify the boundaries of the arterial wall 9 in each of the 2D short-axis cross-sections. For example, the computing device 6 may search radially in the redefined vessel neighborhood for the maximum attenuation gradient in the 2D short-axis cross-sections. In this radial search, the computing device 6 may search only connected voxels having attenuation values in the lower third of the NCP attenuation range (e.g., within a range from the EFT to one third of the NCP upper threshold). Thus, the computing device 6 is searching for voxels having attenuation values greater than epicardial fat "EF" but less than one would expect for the arterial wall 9. To maintain consistency and accuracy, as the computing device 6 searches each 2D short-axis cross-section, the computing device may constrain the search to start from an arterial radius equal to 85% of the arterial radius in the previous, more proximal 2D short-axis cross-section, as suggested by data from previously reported histologic observations. See Taylor A. J., Burke A. P., Farb A., Yousefi P., Malcom G. T., Smialek J., Virmani R., Arterial remodeling in the left coronary system: the role of high-density lipoprotein cholesterol, *J. Am. Coll. Cardiol.*, 1999; 34(3):760-7. Thus, after the arterial wall 9 in the previous, more proximal 2D short-axis cross-section has been segmented, the computing device 6 may fit the arterial wall 9 may be fit to a circle to obtain an arterial radius value for the previous 2D short-axis cross-section.

Because contrast enhancement in the plaques 11A and 11B is expected, an outermost maximal radial gradient boundary found in each 2D cross-section is used to define the boundary of the arterial wall 9. See Cademartiri et al., (2005), supra; and Halliburton at al., supra. In this manner, the arterial wall is segmented from an innermost portion of the epicardial fat "EF" that was combined with an outermost portion of the arterial wall 9 by the process that constructed the 3D representation of the coronary artery 7A.

Then, an average attenuation value (which may be stored in a variable "aw") corresponding to the arterial wall 9 may be computed. The average attenuation value is calculated across the portion of the coronary artery 7A between the start and end points "$P_S$" and "$P_E$" in 3D. Thus, the average attenuation value is calculated across the plaques 11A and 11B.

In block 185, using a selected one of the 2D short-axis cross-sections, the computing device 6 identifies a NCP seed voxel and/or a CP seed voxel. The NCP seed voxel is within the non-calcified components "NCP" of at least one of the plaques 11A and 11B. The CP seed voxel is within the calcified components "CP" of at least one of the plaques 11A and 11B. By way of a non-limiting example, the 2D short-axis cross-section with the greatest luminal stenosis may be used to identify the NCP seed voxel and/or the CP seed voxel. Stenosis may be calculated for the coronary artery 7A in each short-axis cross-section using a method described in Cheng, et al., *JACC Cardiovascular Imaging* 2008; 1; 460-471.

To locate the NCP seed voxel in the selected 2D short-axis cross-section, the computing device 6 searches for a voxel having an attenuation value within a NCP range. The NCP range may be defined as extending from the average attenuation value to the NCP upper threshold. In other words, voxels having attenuation values greater than the average attenuation value of the arterial wall 9 but less than the NCP upper threshold, are presumed to be (and later classified as) non-calcified components "NCP" of one or more of the plaques 11A and 11B.

To locate a CP seed voxel, the computing device 6 searches for a voxel having an attenuation value greater than the CP lower threshold (which was set to the upper contrast level ("u")). In other words, voxels having attenuation values greater than the CP lower threshold are presumed to be (and later classified as) calcified components "CP" of one or more of the plaques 11A and 11B.

If neither a CP nor NCP seed voxel is found, the computing device 6 iteratively searches for (1) a NCP seed voxel by looking for the nearest unclassified voxel having an attenuation value within the NCP attenuation range, and/or (2) a CP seed voxel by looking for the nearest unclassified voxel having an attenuation value greater than the CP lower threshold.

In block 190, the computing device 6 automatically classifies the non-calcified and calcified components "NCP" and "CP" within the arterial wall 9. By way of a non-limiting example, the computing device 6 may perform an iterative, recursive 3D region growing algorithm that expands from each starting NCP seed voxel and/or CP seed voxel (similar to an expanding 3D balloon). 3D region growing is performed recursively until all connected voxels within the applicable attenuation range are identified.

For example, starting from the NCP seed voxel, the computing device 6 may classify any voxel connected (i.e., immediately adjacent) to the NCP seed voxel having an attenuation value within the NCP range as a non-calcified component. Then, any voxels connected to the voxels classified as non-calcified components that also have attenuation values within the NCP range are classified as non-calcified components, and so forth. In this manner, contiguous voxels having attenuation values within the NCP range are identified and classified as non-calcified components of a plaque (e.g., the plaque 11A, plaque 11B, and the like). Thus, discrete (or separated) regions of non-calcified components may be identified and their size (e.g., volumes) determined.

Similarly, starting from the CP seed voxel, the computing device 6 may classify any voxel connected (i.e., immediately adjacent) to the CP seed voxel having an attenuation value greater than the CP lower threshold as a calcified component. Then, any voxels connected to the voxels classified as calcified components, that also have attenuation values greater than the CP lower threshold are classified as calcified components, and so forth. In this manner, contiguous voxels having attenuation values greater than the CP lower threshold are identified and classified as calcified components of a plaque (e.g., the plaque 11A, plaque 11B, and the like). Thus, discrete (or separated) regions of calcified components may be identified and their size (e.g., volumes) determined.

The classified voxels may be weighted (e.g., by a constraint). For example, an independent constraint may be applied to the gradient of the attenuation values to limit the size of the regions classified. The training group was tested with a constraint that the attenuation gradient is required to be less than or equal to 50% in each plaque component. In other words, the attenuation gradient may be constrained to being less than or equal to about 50%.

After a region of contiguous voxels (classified as either non-calcified or calcified components) has been grown, the computing device 6 may continue to look for NCP and CP seed voxels until no more are present in the region of the coronary artery 7A between the start and end points "$P_S$" and "$P_E$."

The various segmented structures (e.g., the lumen 10 or blood "B," the arterial wall 9, and the epicardial fat "EF") may each be displayed using a different color. Further, some structures (e.g., the lumen 10 or blood "B," and the epicardial fat "EF") may be removed from the displayed 3D or 2D representations of the CCTA scan data to provide a better view of other structures (e.g., the arterial wall 9, the non-calcified components "NCP," and the calcified components "CP").

In optional block 195, the classified voxels may be displayed with a color-coded overlay. For example, voxels classified as non-calcified components may be displayed using a first color and voxels classified as calcified components may be displayed using a second color.

In optional block 197, a NCP volume, a CP volume, and/or a plaque composition (e.g., a percentage of non-calcified components versus a percentage of calcified components within one or more of the plaques 11A and 11B) may be calculated and optionally displayed. The NCP volume may be determined as a function of the number of voxels classified as non-calcified components and a volume value corresponding to each voxel. Similarly, CP volume may be determined as a function of the number of voxels classified as calcified components and a volume value corresponding to each voxel.

Then, the method 100 terminates.

Study

From a database of CCTA studies acquired in the current and previous studies, 24 consecutive patients who underwent CCTA, with focal plaques in the proximal and mid segments of the coronary arteries with minimum proximal-to-distal plaque length of 2 mm, were identified. A summary of patient characteristics is shown in Table 1 (below).

TABLE 1

| Patient Characteristic | Value |
| --- | --- |
| No. of patients | 24 |
| Women/men, n/n | 5/24 |
| Age, y, mean ± SD (range) | 64.5 ± 10.1 (47-83) |
| Body Mass Index ("BMI"), kg/m$^2$, mean ± SD (range) | 26.5 ± 3.6 (21-31) |
| Hypertension | 15/24 |
| Diabetes mellitus | 2/24 |
| Current smoker | 7/24 |
| Coronary calcium score, mean ± SD (range) | 478 ± 519 (0-1792.0) |
| Symptomatic (chest pain, shortness of breath, or both) | 14/24 |

The patients underwent CCTA for clinical reasons on a Siemens Definition Dual-Source 64-slice CT scanner (Siemens Medical Solutions, Forcheim, Germany) with gantry rotation time of 330 milliseconds and detector collimation of 0.6 mm. The imaging protocol has previously been described in detail. See Dey, et. al. (2008), supra. Intravenous contrast (80 mL) was administered during each scan. Raw data was reconstructed from 65%-80% of the cardiac cycle in 5% increments, using 0.6-mm slice thickness, 0.3-mm slice increment, single segment reconstruction, a medium-smooth reconstruction kernel (B26f), 512×512 matrix size, and voxel size of 0.4×0.4×0.3 mm. Reconstructed CCTA images were clinically assessed on a Siemens Leonardo workstation as previously described. Id. Image quality for all the scans was excellent to good (5 and 4 on our 1-5 image quality scale). Id. The best phase of the cardiac cycle for visualization of coronary arteries was determined by an expert reader at the time of clinical assessment, and DICOM images corresponding to this phase were transferred to a research workstation for plaque quantification. In addition, as part of our standard protocol, all patients underwent a non-contrast CT scan for coronary calcium scoring, and the Agatston coronary calcium score was quantified on a Sci-Image workstation. See Id.; and Agatston, et al., supra.

Using CCTA scan data obtained for the test subjects described above, results obtained by an implementation of the method 100 were studied and compared to results obtained by (1) a manual quantification technique and (2) interactive threshold adjustment ("ITA.") In the study, 29 plaques were evaluated using the three techniques.

Manual Quantification

Each plaque was independently manually quantified by two experienced readers (V.Y.C., R.N.), blinded to each other, using Vitrea workstation (Vital Images, Minnetonka, Minn.) version 4.1.1. The manual 3D plaque outlining method was similar to previously reported study. Cademartiri, et al. (2005), supra. Standard CTA window width and level settings (width, 800-900 HU; level, 250-300 HU) were initially used, and the reader could modify these settings as needed, particularly when quantifying CP lesions. After identification of a plaque in standard transverse images, serial oblique multiplanar reformatted ("MPR") images orthogonal to the longitudinal axis of the involved vessel segment and the plaque were displayed. The 3D step increment (typically between 0.3 and 0.45 mm) for each cross-sectional segment along the longitudinal axis was calculated by marking the starting and ending positions of the plaque, computing the 3D vector from the start to the end, and dividing the 3D vector by the number of cross-sectional plaque segments. Plaque areas were then manually traced in each cross-sectional segment, and the total NCP and CP volumes were calculated by multiplying the corresponding total plaque areas with the 3D step increment. In total, 798 and 849 2D cross-sectional segments were manually traced by the two observers.

ITA

Each plaque was quantified with plaque analysis software (SUREPlaque; Vital Images) by one of the expert readers (V.Y.C.), by visually adjusting attenuation thresholds for each plaque. Curved multi-planar reformatted ("CMPR") images were rendered and displayed using software. In three cases, an additional manual operation, editing of the centerline to obtain appropriate CMPR display, was necessary. The reader marked starting and ending positions of each plaque in the CMPR display and adjusted attenuation thresholds for non-calcified and calcified components and to match a visual impression of plaque components. These manually determined threshold values were used to obtain the NCP, CP, and total plaque volumes.

Interobserver Variability

The variability between two independent observers for the implementation of the method 100 and ITA were determined. For the implementation of the method 100, each observer independently marked the proximal and distal limits of the plaque (e.g., by inputting the start and end points "$P_S$" and "$P_E$") and drew the "normal blood pool" region(s) of interest. For ITA, each observer independently marked the proximal and distal limits of the plaque and visually adjusted the attenuation thresholds.

Statistical Analysis

The results of plaque quantification were analyzed by Analyse-It software (www.analyse-it.com). All continuous variables were expressed as mean±standard deviation ("SD"). To compare agreements of any two plaque quantification methods, Pearson's correlation coefficient was calculated and Bland-Altman plots were created. Paired t-test was used to compare the difference from manual quantification. A P-value of less than 0.05 was considered statistically significant.

Results of Study

Study processing times ranged from 5 to 25 minutes for manual quantification, from one to three minutes for ITA. The average length of the quantified plaques was 10.2±4.5 mm (range, 2.7-24.8 mm). For manual quantification, the number of short-axis cross-sectional segments that needed to be traced ranged from 9 to 61 per plaque. The time for automated plaque segmentation and quantification was less than two seconds for all plaques in this study on a standard Windows 2.5 GHz computer.

Strong correlation was observed between the two expert readers for NCP volumes (r=0.99, P<0.0001) and for CP volumes (r=0.85, P<0.0001). The 95% limits of agreement range between the two observers were −25.9 to 23.2 mm$^3$ for the non-calcified components and −15.5 to 23.4 mm$^3$ for the calcified components, with a small positive bias (3.96 mm$^3$) for the calcified components. Mean absolute differences between the two readers were 8.4 6 9.6 mm$^3$ for NCP volumes and 6.2±8.7 mm$^3$ for CP volumes.

Attenuation values (in HU) obtained by the study for 29 plaques are displayed in Table 2. Table 2 includes the EFT value, the NCP upper threshold, and the CP lower threshold obtained for 29 plaques by the study. Table 2 also includes the attenuation value for the normal blood (lumen) at the middle 2D cross-section (which is labeled "Mid-lesion normal contrast").

TABLE 2

| Attenuation values (in HU) | Values (mean ± SD (range)) |
|---|---|
| EFT value, | −16 ± 13 (−3 to −41) |
| NCP upper threshold | 227 ± 40 (145-335) |
| CP lower threshold | 511 ± 80 (397-689) |
| Mid-lesion normal contrast | 419 ± 78 (333-618) |

Figure 5:
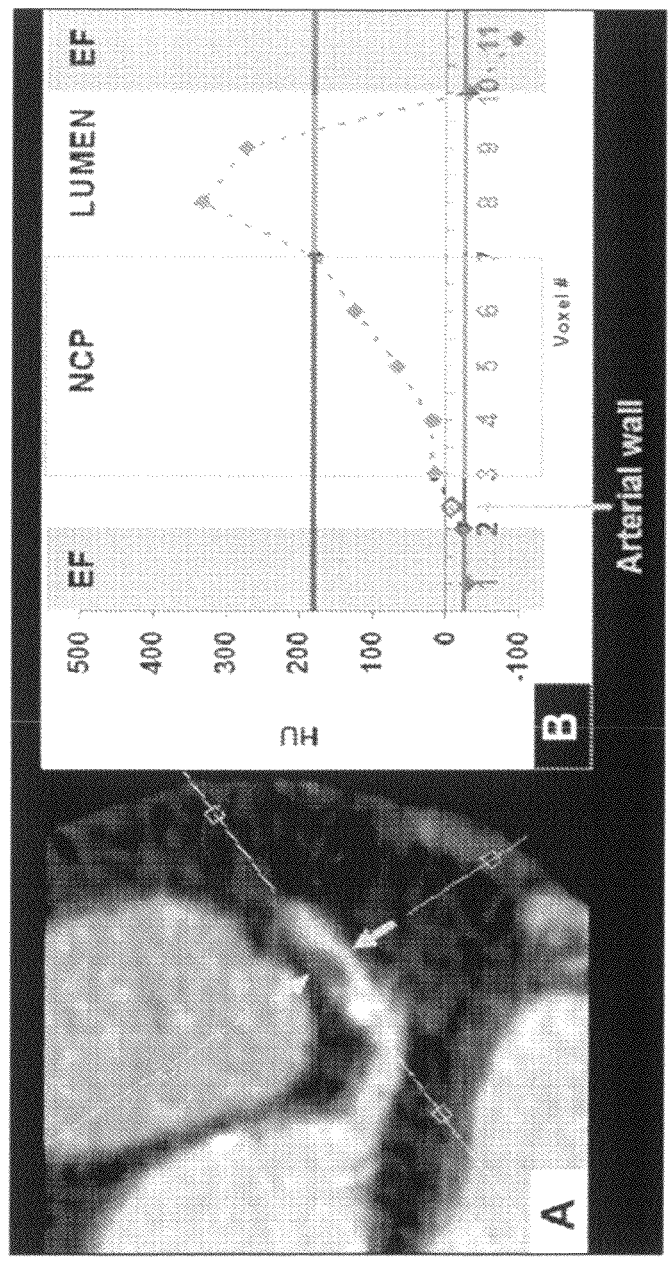
FIG. 5 depicts (1) a longitudinal cross-sectional image generated from CCTA scan data along a left hand side, and (2) along a right hand side, a graph plotting attenuation values (as an attenuation profile) through a mid-plaque short-axis cross-sectional plane identified by arrows on the longitudinal cross-sectional image.

Along the left hand side, FIG. 5 depicts a longitudinal cross-sectional image generated from CCTA scan data depicting a plaque having both non-calcified and calcified components. Along the right hand side, FIG. 5 depicts a graph plotting attenuation values (as an attenuation profile) through a mid-plaque short-axis cross-sectional plane. This plane is identified by arrows on the longitudinal cross-sectional image (along the left hand side of FIG. 5). The x-axis of the graph is voxel number and the y-axis is attenuation value (in HU). The epicardial fat "EF," non-calcified components "NCP," and lumen 10 are identified by vertical bands (identifying pixel numbers) in the attenuation profile graph. For this dataset, the method 100 determined the upper NCP threshold to be 180 HU (identified by an upper horizontal line), and the EFT value to be 220 HU (identified by a lower horizontal line). The arterial wall 9 is identified by a larger diamond and an arrow pointing to the larger diamond. The corresponding attenuation value at the larger diamond is −10 HU.

Figure 6:
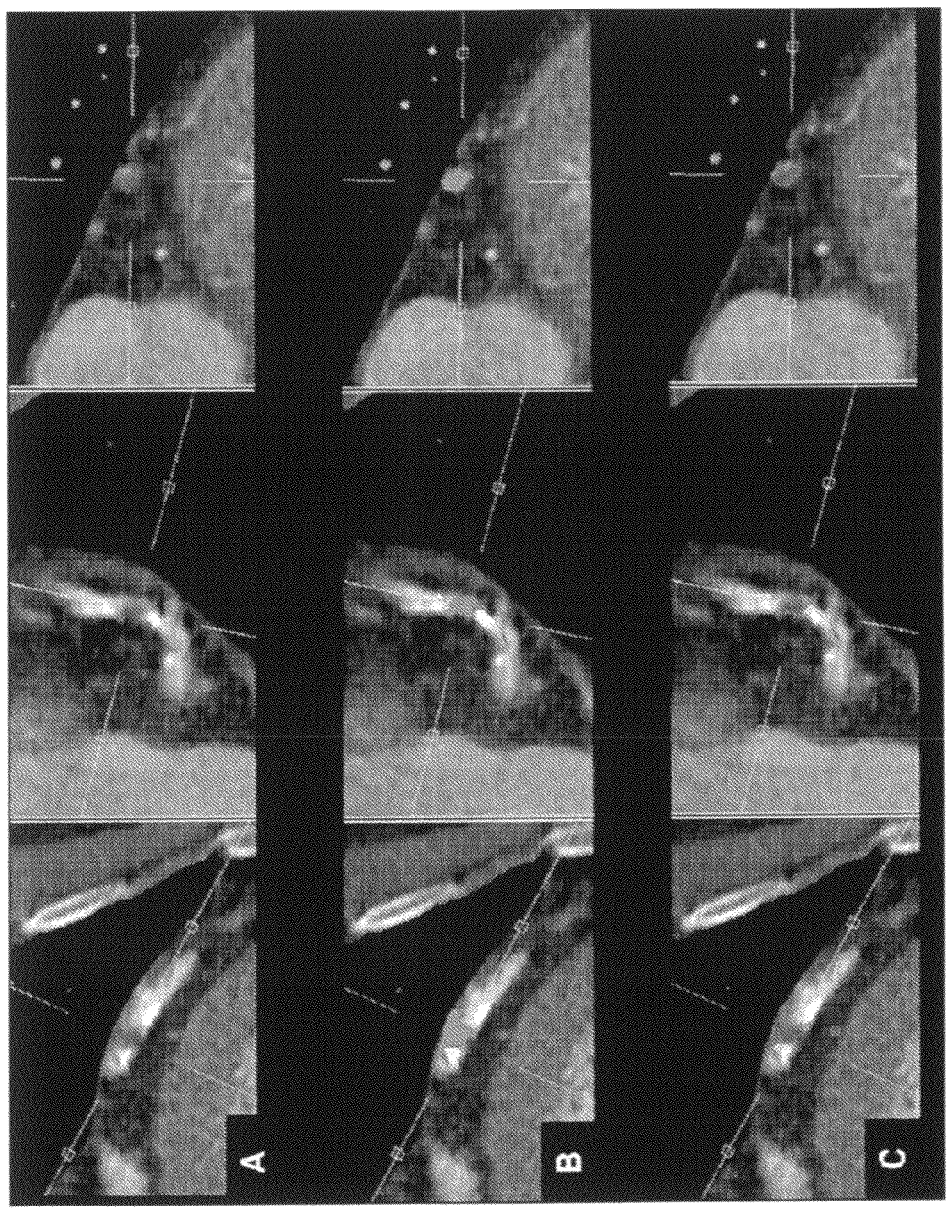
FIG. 6 is a series of images (generated from CCTA scan data) depicting results obtained from an implementation of the method of FIG. 4 when performed on a mid-left anterior descending ("mid-LAD") coronary artery plaque for a 51-year-old male smoker.
Figure 7:
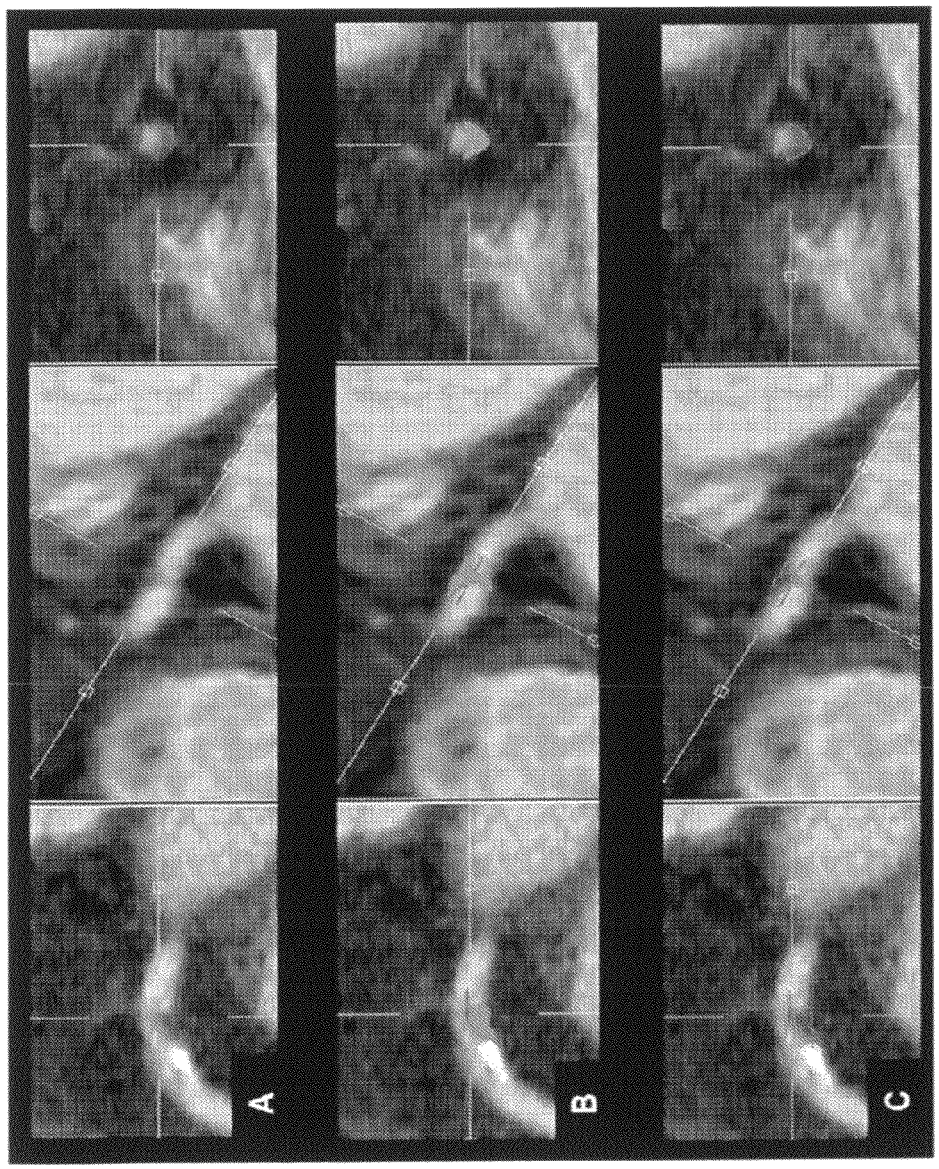
FIG. 7 is a series of images (generated from CCTA scan data) depicting results obtained from an implementation of the method of FIG. 4 when performed on a curved proximal right coronary artery ("RCA") plaque for a 66-year-old symptomatic male patient.

Examples of two lesions quantified using the method 100 are shown in FIGS. 6 and 7.

FIG. 6 is a series of images (generated from CCTA scan data) depicting the results of the method 100 for a mid-left anterior descending ("mid-LAD") coronary artery plaque for a 51-year-old male smoker having a coronary calcium score of 761. His maximum heart rate during the CCTA scan was 80 beats/min (image quality good). The topmost row of images in FIG. 6 depict MPR views showing a curved mixed plaque from the mid-LAD coronary artery. The middle row of image in FIG. 6 depicts a color-coded overlay (determined using the method 100), with in which the calcified components are identified using a contour having a first color (e.g., yellow) and the non-calcified components are identified using a contour having a second color (e.g., red). The bottommost row of images in FIG. 6 depicts an overlay in which the non-calcified components are identified using a contour having a first color (e.g., red) and the calcified components are identified using a contour having a second color (e.g., yellow). For this lesion, the method 100 calculated an NCP volume of about 75.8 mm$^3$ and a CP volume of about 14.4 mm$^3$, with about 88% stenosis. The mean±standard deviation within the non-calcified component was about 81.4±58.3 HU. Quantitative coronary angiography determined the percentage of stenosis to be about 67%.

FIG. 7 is a series of images (generated from CCTA scan data) depicting the results of the method 100 for a curved proximal right coronary artery ("RCA") plaque for a 66-year-old symptomatic male patient having a coronary calcium score of 979. His maximum heart rate during the CCTA scan was 50 beats/min (image quality excellent). The topmost row of images in FIG. 7 depicts MPR views showing a curved mixed plaque from the mid-LAD coronary artery. The middle row of images in FIG. 7 depicts a color-coded overlay (determined using the method 100), with in which the calcified components are identified using a contour having a first color (e.g., yellow) and the non-calcified components are identified using a contour having a second color (e.g., red). The bottommost row of images in FIG. 7 depicts an overlay in which the non-calcified components are identified using a contour having a first color (e.g., red) and the calcified components are identified using a contour having a second color (e.g., yellow). For this lesion, the method 100 calculated an NCP volume of about 43 mm$^3$ and a CP volume of about 14.4 mm$^3$, with about 31% stenosis. The mean±standard deviation within the non-calcified component was about 96±59 HU.

For the non-calcified components "NCP," the method 100 achieved a significantly lower mean absolute difference from expert readers than for ITA (the method 100, 26.7±21.2 mm$^3$; ITA, 42.1±34.8 mm$^3$; P=0.01). For the calcified components, the method 100 also achieved a significantly lower mean absolute difference from expert readers than for ITA (the method 100, 6.0±5.5 mm$^3$; ITA, 30.5±22.5 mm$^3$; P<0.0001).

Figure 8A:
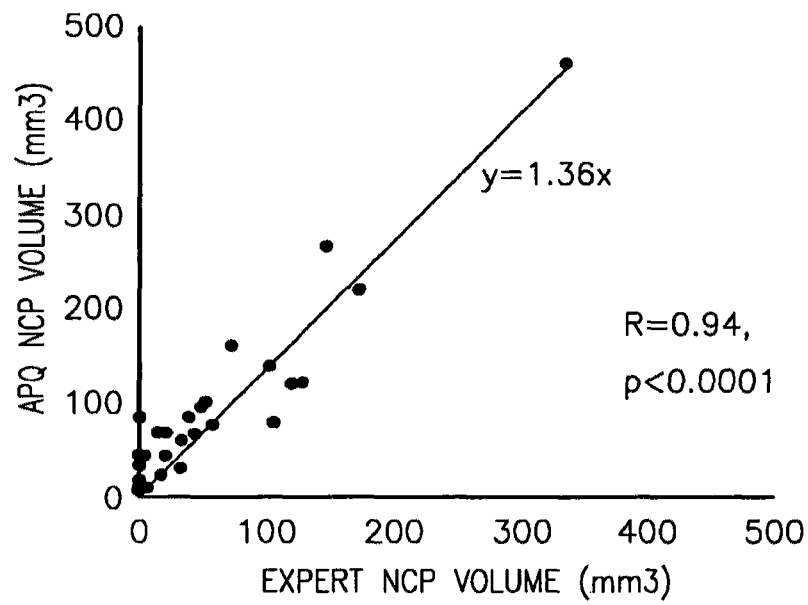
FIG. 8A is plot of a correlation between a volume of non-calcified plaque components determined by an implementation of the method of FIG. 4 and a volume of non-calcified plaque components determined manually and averaged between the two experts.
Figure 8B:
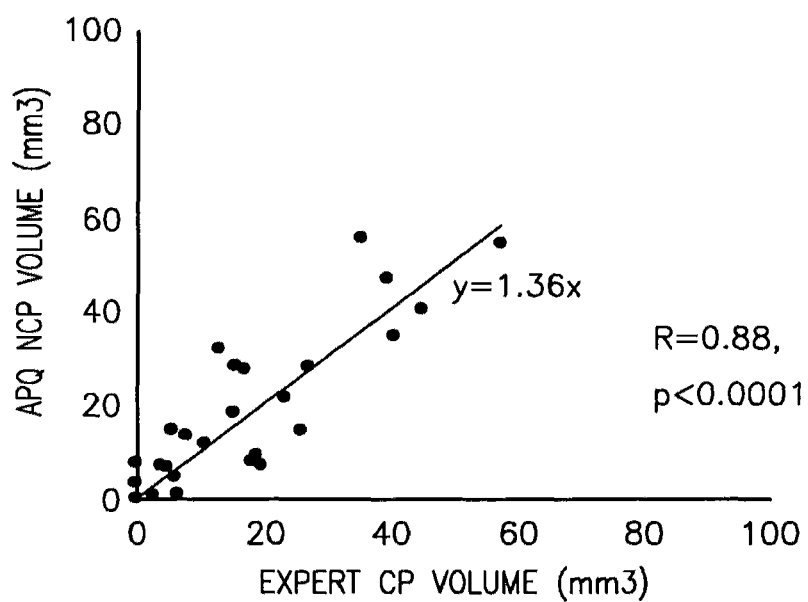
FIG. 8B is plot of a correlation between a volume of calcified plaque components determined by an implementation of the method of FIG. 4 and a volume of calcified plaque components determined manually and averaged between the two experts.
Figure 8C:
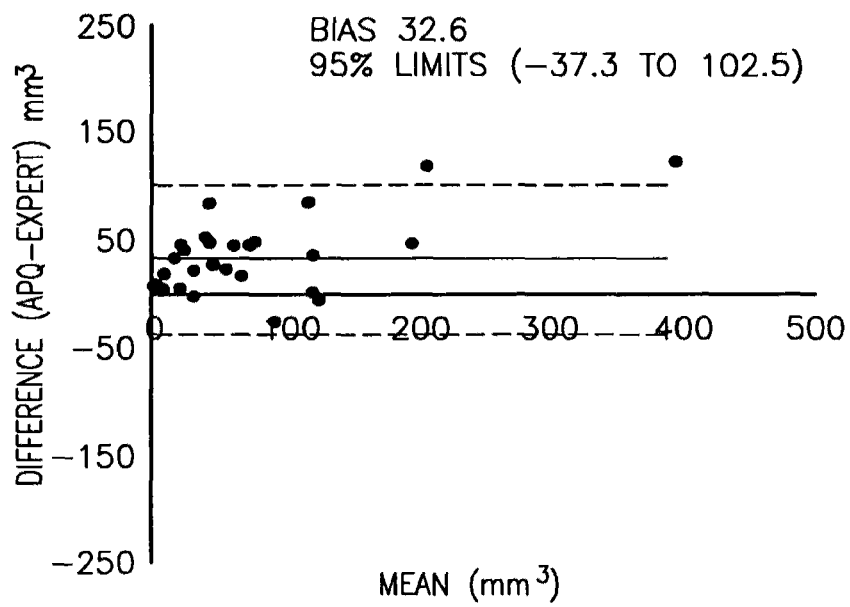
FIG. 8C is plot of a Bland-Altman comparison between the volume of non-calcified plaque components determined by an implementation of the method of FIG. 4 and the volume of non-calcified plaque components determined manually and averaged between the two experts.
Figure 8D:
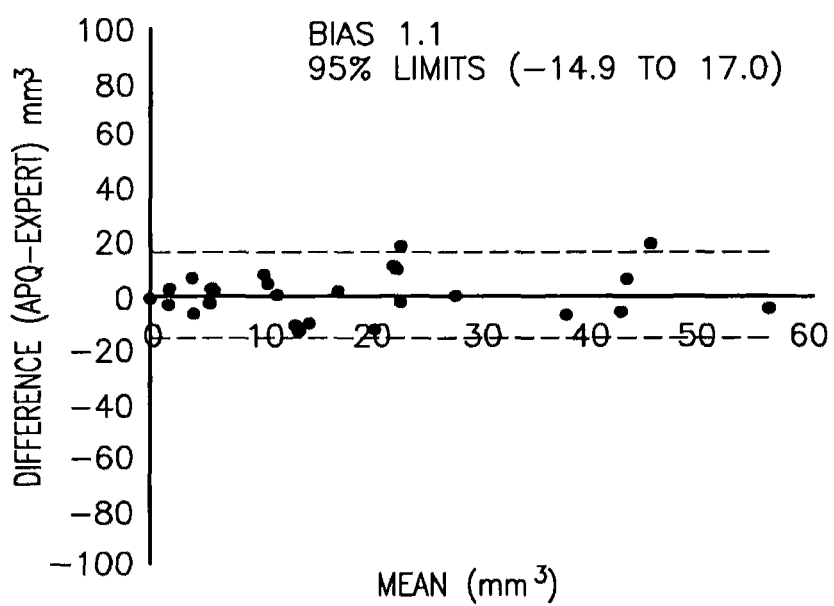
FIG. 8D is plot of a Bland-Altman comparison between the volume of calcified plaque components determined by an implementation of the method of FIG. 4 and the volume of calcified plaque components determined manually and averaged between the two experts.

In FIGS. 8A-8D and 9A-9D, the method 100 is identified as "APQ." Correlation between NCP volume determined by the method 100 and NCP volume determined manually and averaged between the two experts is shown in FIG. 8A. Bland-Altman comparisons of the NCP volume determined by the method 100, and the NCP volume determined manually and averaged between the two experts, are shown in FIG. 8C. Correlation between CP volume determined by the method 100 and CP volume determined manually and averaged between the two experts is shown in FIG. 8B. Bland-Altman comparisons of the CP volume determined by the method 100, and the CP volume determined manually and averaged between the two experts, are shown in FIG. 8D.

As may be seen in FIG. 8A, the correlation coefficient for NCP volume was about 0.94 (P<0.0001). As may be seen in FIG. 8A, the correlation coefficient for CP volume was about 0.88 (P<0.0001). Best-fit lines for the data (represented by the equations y=1.36× for NCP volume and y=1.005× for CP volume) are shown in FIGS. 8A and 8B. Referring to FIG. 8C, for NCP volume, there was a positive bias of 32.6 mm$^3$, and the 95% limits of agreement were −37.3 to 102.5 mm$^3$. Referring to FIG. 8D, for CP volume, there was a small positive bias of 1.1 mm$^3$, and the 95% limits of agreement were −14.9 to 17.0 mm$^3$.

Figure 9A:
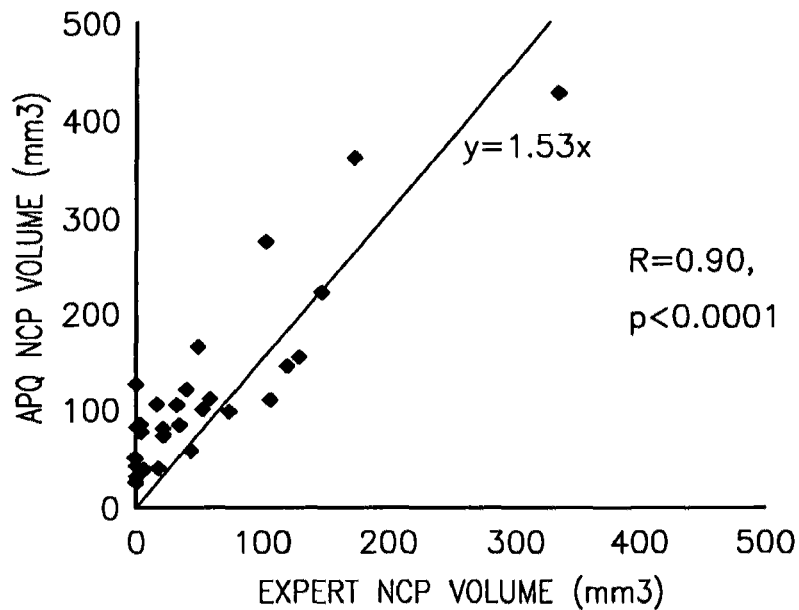
FIG. 9A is plot of a correlation between a volume of non-calcified plaque components determined using interactive threshold adjustment ("ITA") and the volume of non-calcified plaque components determined manually and averaged between the two experts.
Figure 9B:
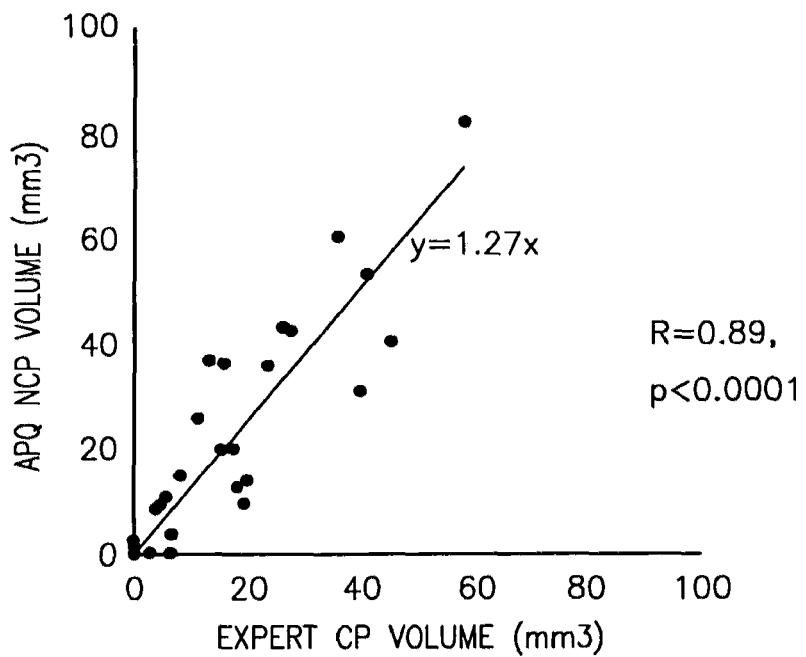
FIG. 9B is plot of a correlation between a volume of calcified plaque components determined using interactive threshold adjustment ("ITA") and the volume of calcified plaque components determined manually and averaged between the two experts.
Figure 9C:
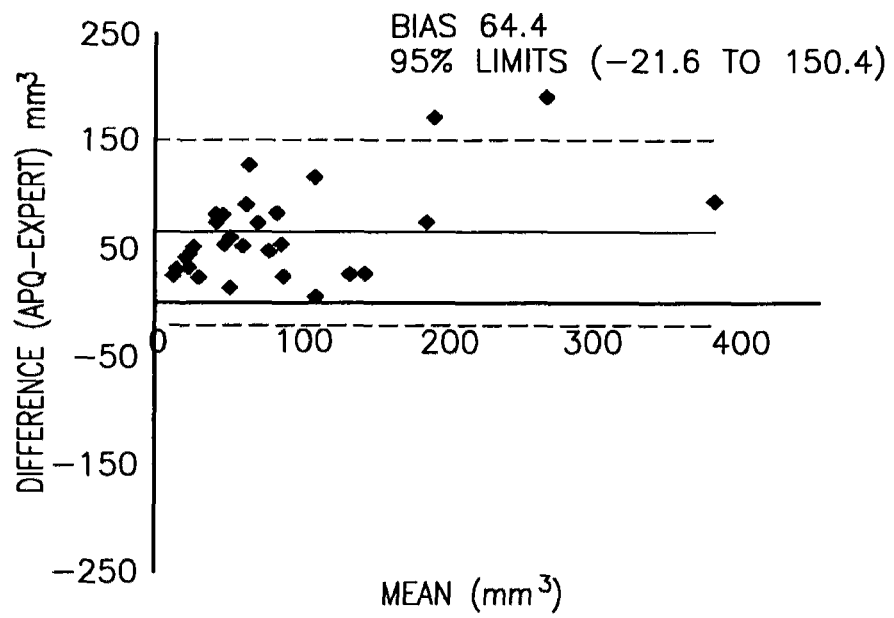
FIG. 9C is plot of a Bland-Altman comparison between the volume of non-calcified plaque components determined using ITA and the volume of non-calcified plaque components determined manually and averaged between the two experts.
Figure 9D:
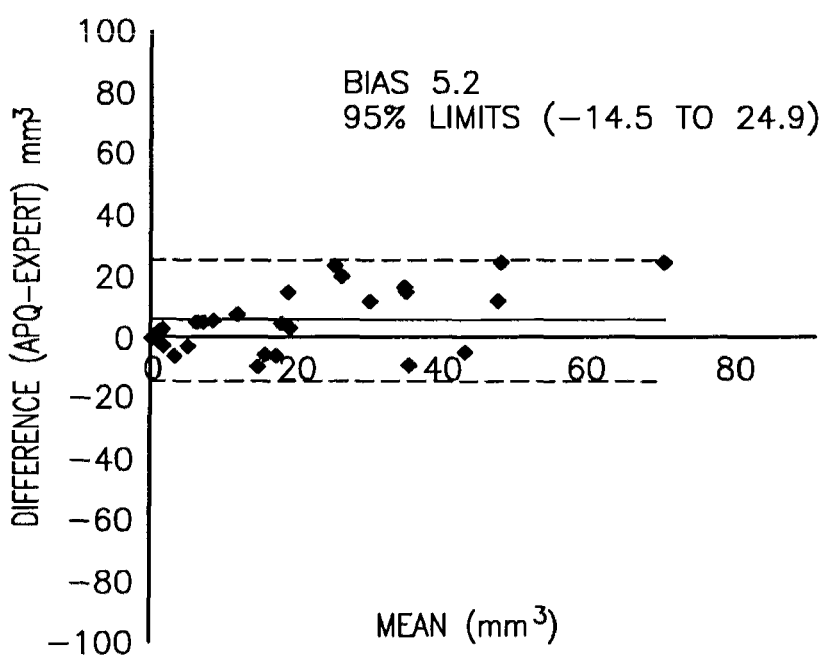
FIG. 9D is plot of a Bland-Altman comparison between the volume of calcified plaque components determined using ITA and the volume of calcified plaque components determined manually and averaged between the two experts.

Correlation between NCP volume determined by ITA and NCP volume determined manually and averaged between the two experts is shown in FIG. 9A. Bland-Altman comparisons of NCP volume determined by ITA, and NCP volume determined manually and averaged between the two experts, are shown in FIG. 9C. The correlation of the CP volume determined by ITA and CP volume determined manually and averaged between the two experts is shown in FIG. 9B. Bland-Altman comparisons of the CP volume determined by ITA, and CP volume determined manually and averaged between the two experts, are shown in FIG. 9D.

As may be seen in FIG. 9A, the correlation coefficient for NCP volume was 0.90 (P<0.0001). As may be seen in FIG. 9B, the correlation coefficient for CP it was 0.89 (P<0.0001). Best-fit lines for the data (represented by the equations y=1.53× for NCP volume, and y=1.27× for CP volume) are shown in FIGS. 9A and 9B. Referring to FIG. 9C, for NCP volume, there was a positive bias of 64.4 mm$^3$, and the 95% limits of agreement were −21.6 to 150.4 mm$^3$. Referring to FIG. 9D, for CP volume, there was a small positive bias of 5.2 mm$^3$, and the 95% limits of agreement were −14.5 to 24.9 mm$^3$.

For the non-calcified components "NCP," the method 100 achieved a significantly lower bias than ITA (32.6 mm$^3$ versus 64.4 mm$^3$) and tighter 95% limits of agreement (P=0.01). Because of routine inclusion of the arterial wall 9 and the epicardial fat "EF" in the non-calcified components, ITA overestimated the non-calcified components in both normal and abnormal plaque cross-sections, as previously reported in Akram, et al., supra. Using the method 100, overestimation of the non-calcified components was primarily found in abnormal cross-sections. For the calcified components, the method 100 also achieved a significantly lower bias than did ITA (1.1 mm$^3$ versus 5.2 mm$^3$) and tighter 95% limits of agreement (P<0.0001). Correlation with expert manual quantification for the classification of the non-calcified components was higher for the method 100 than for ITA (0.94 versus 0.90 for NCP volume). For plaque composition, there was excellent correlation between the method 100 and the expert readers (r=0.90, P<0.0001 for both percentage of NCP and percentage of CP volume), and between ITA and the expert readers (r=0.95, P<0.0001).

Visually, the method 100 was visually assessed to be successful (extending over the entire non-calcified and calcified components and without missing a voxel) in all 29 plaques, with some overestimation of the non-calcified components because of the inclusion (or classification) of artifactual low attenuation value beam-hardening areas as non-calcified components "NCP," and the inclusion (or classification) of a portion of the epicardial fat "EF" as non-calcified components "NCP," especially for small plaque lesions located at vessel branch points.

An overall limitation of the manual plaque quantification technique is that while adding plaque component areas from the serial MPR images is accurate for plaques with linear configuration; this technique only approximates true plaque volumes for curved or tortuous plaques. In this study, 3 of 29 plaques were curved plaques. A curved proximal RCA plaque is shown in FIG. 7.

Computing Device

Figure 10:
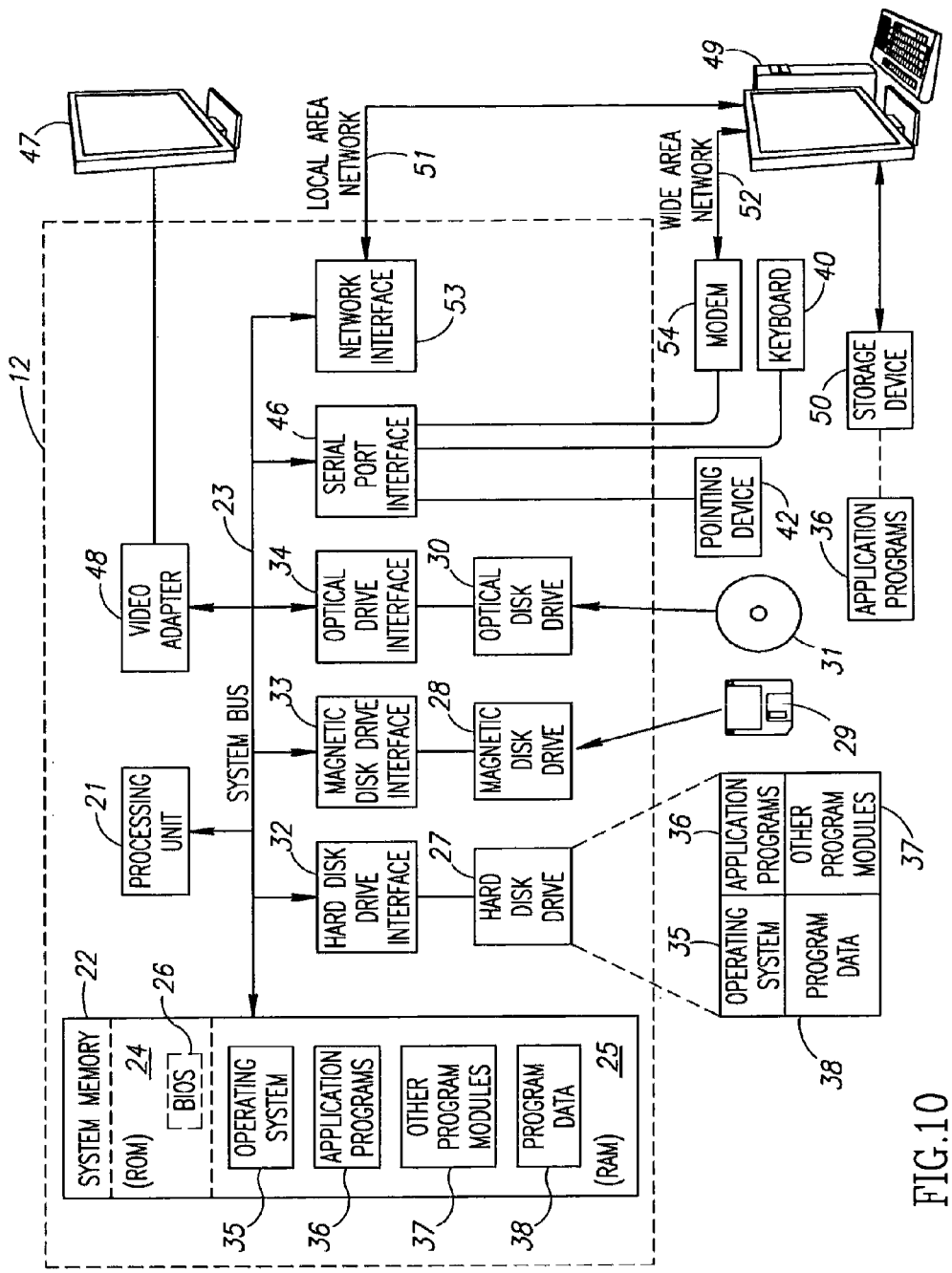
FIG. 10 is a diagram of a hardware environment and an operating environment in which the computing device of FIG. 1 may be implemented.

FIG. 10 is a diagram of hardware and an operating environment in conjunction with which implementations of the computing device 6 may be practiced. The description of FIG. 10 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multiprocessor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 10 includes a general-purpose computing device in the form of a computing device 12. The computing device 6 may each be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like.

The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 104 (illustrated FIG. 1) may be substantially similar to the system memory 21. The system memory 21 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feed back game controller).

The monitor 47 may be used to display a three or 2D representations of CCTA scan data. By way of a non-limiting example, referring to FIG. 1, the monitor 47 (see FIG. 10) may display a 3D and/or 2D visual representation of the CCTA scan data obtained from the scanning device 5.

The input devices described above are operable to receive user input and selections. Together the input and display devices may be described as providing a user interface. The input devices may be used to identify the control points "$P_1$"-"$P_5$," the start point "$P_S$," and/or the end point "$P_E$." Further, the input devices may be used to identify the regions of interest used to determine the normal blood pool in block 115. The user interface may be used by the computing device 6 when executing the APQ module 102 to display the color overlays, the 2D short-axis or longitudinal cross-sections, and/or the 3D representation of the CCTA scan data to an operator.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 10 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

When executed by one or more processors (e.g., the processing unit 21), the APQ module 102 may cause the one or more processors to perform all or portions of the method 100. Further, the system memory 104 may store instructions that when executed by one or more processors, instruct the scanning device 5 to perform a CCTA scan.

Any of the instructions described above, including the instructions of the module 102, may be stored on one or more non-transitory computer-readable media. The instructions described above are executable by one or more processors (e.g., the processing unit 21) and when executed perform the functions described above.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A computer implemented method comprising:
obtaining cardiac computed tomography angiography ("CCTA") scan data comprising a plurality of attenuation values, the CCTA scan data imaging a pool of blood, and a coronary artery having a lumen defined by an artery wall at least partially surrounded by epicardial fat;
receiving an identification of a first portion of the plurality of attenuation values, the first portion being located within the pool of blood;
receiving identifications of a plurality of points positioned within the lumen of the coronary artery;
determining a calcified component threshold based at least in part on the first portion of the plurality of attenuation values;
generating one or more centerlines from the plurality of points;
determining a vessel neighborhood based on the one or more centerlines;
generating a series of short-axis cross-sections through the coronary artery based on the one or more centerlines, each of the short-axis cross-sections comprising a point positioned on one of the one or more centerlines;
within each of the series of short-axis cross-sections, identifying at least one epicardial fat region within the vessel neighborhood;
determining an epicardial fat threshold ("EFT") value based on ones of the plurality of attenuation values within the epicardial fat regions identified within each of the series of short-axis cross-sections;
within each of the series of short-axis cross-sections, classifying portions of the short-axis cross-section having attenuation values below the EFT value as epicardial fat;
determining a non-calcified component threshold based at least in part on the first portion of the plurality of attenuation values;
classifying as lumen a connected portion of CCTA scan data adjacent the one or more centerlines and having attenuation values greater than the non-calcified component threshold and less than the calcified component threshold;
within each of the series of short-axis cross-sections, detecting an outer boundary of the coronary artery in the short-axis cross-section, and classifying as arterial wall a portion of CCTA scan data positioned between the outer boundary of the coronary artery and the portion classified as lumen;
determining an artery wall value as a function of the ones of the attenuation values located within the portion of the CCTA scan data classified as arterial wall;
identifying at least one of a non-calcified component seed element and a calcified component seed element in the portion classified as arterial wall;
for each non-calcified component seed element identified, classifying as non-calcified components any portions of the CCTA scan data continuous with the non-calcified component seed element and having attenuation values that are greater than the artery wall value and less than the non-calcified component threshold value; and
for each calcified component seed element identified, classifying as calcified components any portions of the CCTA scan data continuous with the calcified component seed element and having attenuation values that are greater than the calcified component threshold value.

2. The method of claim 1, further comprising:
displaying at least a portion of the CCTA scan data with an overlay identifying one or more portions of the CCTA scan data classified as calcified components and one or more portions of the CCTA scan data classified as non-calcified components.

3. The method of claim 1, further comprising at least one of:
determining a non-calcified plaque volume for at least one portion of the CCTA scan data classified as non-calcified components, and
determining a calcified plaque volume for at least one portion of the CCTA scan data classified as calcified components.

4. The method of claim 1, wherein the artery wall value is an average of ones of the attenuation values located within the portion of the CCTA scan data classified as arterial wall.

5. The method of claim 1, wherein detecting the outer boundary of the coronary artery in each of the series of short-axis cross-sections comprises:
detecting, relative to the point positioned on one of the one or more centerlines, an outermost and maximum radial gradient boundary.

6. The method of claim 1, wherein detecting the outer boundary of the coronary artery in each of the series of short-axis cross-sections comprises:
detecting, relative to the point positioned on one of the one or more centerlines, an outermost and maximum radial gradient boundary located within portions of the CCTA scan data having attenuation values greater than the EFT value but significantly less than the non-calcified component threshold value.

7. The method of claim 1, further comprising:
within each of the series of short-axis cross-sections, identifying attenuation values within the lumen of the coronary artery, and determining a normal contrast value based on the attenuation values identified as being within the lumen of the coronary artery; and
determining a lower contrast level based on the first portion of the plurality of attenuation values, wherein the non-calcified component threshold is determined as a function of the lower contrast level and the normal contrast value of a selected one of the series of short-axis cross-sections.

8. The method of claim 7, wherein within each of the series of short-axis cross-sections, determining the normal contrast value further comprises:

determining a minimum attenuation value within the first portion of the plurality of attenuation values;

growing a region from the point positioned on one of the one or more centerlines to include any portions of the CCTA scan data contiguous with the point and having attenuation values greater than the minimum attenuation value and less than the non-calcified component threshold value; and determining the normal contrast value as a function of the attenuation values within the region grown from the point positioned on one of the one or more centerlines.

9. The method of claim 7, further comprising:

determining whether the lumen of the coronary artery is completely occluded;

if it is determined that the lumen of the coronary artery is completely occluded, selecting a distal one of the series of short-axis cross-sections as the selected one of the series of short-axis cross-sections; and if it is determined that the lumen of the coronary artery is not completely occluded, selecting a middle one of the series of short-axis cross-sections as the selected one of the series of short-axis cross-sections.

10. The method of claim 1, wherein the calcified component threshold is greater than a mean of the first portion of the plurality of attenuation values.

11. The method of claim 10, wherein the calcified component threshold is equal to a sum of a standard deviation of the first portion of the plurality of attenuation values multiplied by a value greater than one and the mean of the first portion of the plurality of attenuation values.

12. The method of claim 1, wherein the non-calcified component threshold is less than a mean of the first portion of the plurality of attenuation values.

13. The method of claim 12, wherein the non-calcified component threshold is equal to a standard deviation of the first portion of the plurality of attenuation values multiplied by a value greater than one and subtracted from the mean of the first portion of the plurality of attenuation values.

14. The method of claim 13, further comprising:

within each of the series of short-axis cross-sections, identifying attenuation values within the lumen of the coronary artery, and determining a normal contrast value based on the attenuation values identified as being within the lumen of the coronary artery; and determining a lower contrast level based on the first portion of the plurality of attenuation values, wherein the non-calcified component threshold is determined as a function of the lower contrast level and the normal contrast value of a selected one of the series of short-axis cross-sections.

15. The method of claim 1, wherein the one or more centerlines are splines.

16. A computer implemented method for use with cardiac computed tomography angiography ("CCTA") scan data imaging a pool of blood, and a coronary artery having a lumen defined by an artery wall at least partially surrounded by epicardial fat, the method comprising:

constructing a three dimensional representation of the CCTA scan data comprising a plurality of voxels, each voxel being associated with an attenuation value;

receiving an identification a first portion of the plurality of voxels, the first portion being located within the pool of blood;

receiving identifications of a plurality of locations positioned within ones of the plurality of voxels corresponding to the lumen of the coronary artery;

generating one or more lines from the plurality of points;

determining a vessel neighborhood based on the one or more lines;

determining a calcified component threshold based at least in part on attenuation values associated with the first portion of the plurality of voxels;

generating a series of short-axis cross-sections through the three dimensional representation based on the one or more lines, each of the short-axis cross-sections comprising a point positioned on one of the one or more lines;

within each of the series of short-axis cross-sections, identifying at least one epicardial fat region within the vessel neighborhood, determining an epicardial fat threshold ("EFT") value based on the attenuation values associated with ones of the plurality of voxels within the epicardial fat regions identified within each of the series of short-axis cross-sections;

within each of the series of short-axis cross-sections, classifying voxels associated with attenuation values below the EFT value as epicardial fat;

determining a non-calcified component threshold based at least in part on the attenuation values associated with the first portion of the plurality of voxels;

classifying as lumen ones of the plurality of voxels adjacent the one or more lines and associated attenuation values greater than the non-calcified component threshold and less than the calcified component threshold;

within each of the series of short-axis cross-sections, detecting an outer boundary of the coronary artery in the short-axis cross-section, and classifying as arterial wall ones of the plurality of voxels positioned between the outer boundary of the coronary artery and the ones of the plurality of voxels classified as lumen;

determining an artery wall value as a function of the attenuation values associated with ones of the plurality of voxels classified as arterial wall;

identifying at least one of a non-calcified component seed voxel and a calcified component seed voxel in the ones of the plurality of voxels classified as arterial wall;

for each non-calcified component seed voxel identified, classifying as non-calcified components any ones of the plurality of voxels continuous with the non-calcified component seed voxel and associated with attenuation values that are greater than the artery wall value and less than the non-calcified component threshold value; and for each calcified component seed voxels identified, classifying as calcified components any ones of the plurality of voxels continuous with the calcified component seed voxel and associated attenuation values that are greater than the calcified component threshold value.

17. The method of claim 16, further comprising:

displaying a three dimensional representation of the CCTA scan data comprising at least a portion of the plurality of voxels and an overlay identifying at least a portion of the ones of the plurality of voxels classified as calcified components and at least a portion of the ones of the plurality of voxels classified as non-calcified components.

18. The method of claim 16, further comprising at least one of: determining a non-calcified plaque volume for at least a portion of the ones of the plurality of voxels classified as non-calcified components, and determining a calcified plaque volume for at least a portion of the ones of the plurality of voxels classified as calcified components.

19. The method of claim 16, wherein the artery wall value is an average of the attenuation values associated with ones of the plurality of voxels classified as arterial wall.

20. The method of claim 16, wherein detecting the outer boundary of the coronary artery in each of the series of short-axis cross-sections comprises:
detecting, relative to the point positioned on one of the one or more lines, an outermost and maximum radial gradient boundary located within ones of the plurality of voxels associated with attenuation values greater than the EFT value but significantly less than the non-calcified component threshold value.

21. The method of claim 16, further comprising:
within each of the series of short-axis cross-sections, identifying ones of the plurality of voxels located within the lumen of the coronary artery, and determining a normal contrast value based on the attenuation values associated with the ones of the plurality of voxels located within the lumen of the coronary artery; and
determining a lower contrast level based on the attenuation values associated with the first portion of the plurality of voxels, wherein the non-calcified component threshold is determined as a function of the lower contrast level and the normal contrast value of a selected one of the series of short-axis cross-sections.

22. The method of claim 21, wherein within each of the series of short-axis cross-sections, determining the normal contrast value further comprises:
determining a minimum attenuation value within the attenuation values associated with the first portion of the plurality of voxels;
growing a region from the point positioned on one of the one or more lines to include any ones of the plurality of voxels contiguous with the point and associated with attenuation values greater than the minimum attenuation value and less than the non-calcified component threshold value; and
determining the normal contrast value as a function of the attenuation values of the ones of the plurality of voxels within the region grown from the point positioned on the one of the one or more lines.

23. The method of claim 21, further comprising:
determining whether the lumen of the coronary artery is completely occluded;
if it is determined that the lumen of the coronary artery is completely occluded, selecting a distal one of the series of short-axis cross-sections as the selected one of the series of short-axis cross-sections; and
if it is determined that the lumen of the coronary artery is not completely occluded, selecting a middle one of the series of short-axis cross-sections as the selected one of the series of short-axis cross-sections.

24. The method of claim 16, wherein the one or more lines are splines.

25. A system comprising:
means for obtaining cardiac computed tomography angiography ("CCTA") scan data comprising a plurality of attenuation values, the CCTA scan data imaging a pool of blood, and a coronary artery having a lumen defined by an artery wall at least partially surrounded by epicardial fat;
means for receiving an identification a first portion of the plurality of attenuation values, the first portion being located within the pool of blood;
means for receiving identifications of a plurality of points positioned within the lumen of the coronary artery;
means for determining a calcified component threshold based at least in part on the first portion of the plurality of attenuation values;
means for generating one or more lines from the plurality of points; means for determining a vessel neighborhood based on the one or more lines;
means for generating a series of short-axis cross-sections through the coronary artery based on the one or more lines, each of the short-axis cross-sections comprising a point positioned on one of the one or more lines;
within each of the series of short-axis cross-sections, means for identifying at least one epicardial fat region within the vessel neighborhood;
means for determining an epicardial fat threshold ("EFT") value based on ones of the plurality of attenuation values within the epicardial fat regions identified within each of the series of short-axis cross-sections;
within each of the series of short-axis cross-sections, means for classifying portions of the short-axis cross-section having attenuation values below the EFT value as epicardial fat;
means for determining a non-calcified component threshold based at least in part on the first portion of the plurality of attenuation values;
means for classifying as lumen a connected portion of CCTA scan data adjacent the one or more lines and having attenuation values greater than the non-calcified component threshold and less than the calcified component threshold;
within each of the series of short-axis cross-sections, means for detecting an outer boundary of the coronary artery in the short-axis cross-section, and means for classifying as arterial wall a portion of CCTA scan data positioned between the outer boundary of the coronary artery and the portion classified as lumen;
means for determining an artery wall value as a function of the ones of the attenuation values located within the portion of the CCTA scan data classified as arterial wall;
means for identifying at least one of a non-calcified component seed element and a calcified component seed element in the portion classified as arterial wall;
for each non-calcified component seed element identified, means for classifying as non-calcified components any portions of the CCTA scan data continuous with the non-calcified component seed element and having attenuation values that are greater than the artery wall value and less than the non-calcified component threshold value; and
for each calcified component seed element identified, means for classifying as calcified components any portions of the CCTA scan data continuous with the calcified component seed element and having attenuation values that are greater than the calcified component threshold value.

26. The system of claim 25, further comprising:
means for displaying at least a portion of the CCTA scan data, and in the displayed portion, identifying one or more portions of the CCTA scan data classified as calcified components and one or more portions of the CCTA scan data classified as non-calcified components.

27. The system of claim 25, further comprising:
means for determining a non-calcified plaque volume of the portions of the CCTA scan data classified as non-calcified components;
means for determining a calcified plaque volume of the portions of the CCTA scan data classified as calcified components; and means for displaying the non-calcified plaque volume and calcified plaque volume.

28. The system of claim 25, wherein the means for detecting the outer boundary of the coronary artery in each of the series of short-axis cross-sections comprises:
   mean for detecting, relative to the point positioned on one of the one or more centerlines, an outermost and maximum radial gradient boundary located within portions of the CCTA scan data having attenuation values greater than the EFT value but significantly less than the non-calcified component threshold value.

29. The system of claim 25, further comprising:
   within each of the series of short-axis cross-sections, means for identifying attenuation values within the lumen of the coronary artery, and means for determining a normal contrast value based on the attenuation values identified as being within the lumen of the coronary artery; and
   means for determining a lower contrast level based on the first portion of the plurality of attenuation values, wherein the means for determining a non-calcified component threshold comprises means for determining the non-calcified component threshold as a function of the lower contrast level and the normal contrast value of a selected one of the series of short-axis cross-sections.

30. The system of claim 29, further comprising:
   means for determining whether the lumen of the coronary artery is completely occluded; and
   means for selecting the selected one of the series of short-axis cross-sections based on whether the means for determining whether the lumen of the coronary artery is completely occluded determines the lumen is completely occluded.

31. The system of claim 30, wherein
   the means for selecting the selected one of the series of short-axis cross-sections selects a distal one of the series of short-axis cross-sections when the means for determining whether the lumen of the coronary artery is completely occluded determines the lumen is completely occluded; and
   the means for selecting the selected one of the series of short-axis cross-sections selects a middle one of the series of short-axis cross-sections when the means for determining whether the lumen of the coronary artery is completely occluded determines the lumen is not completely occluded.

32. The system of claim 25, wherein the one or more lines are centerlines constructed from splines.

33. Non-transitory computer readable media comprising instructions executable by one or more processors and when executed by the one or more processors causing the one or more processors to perform a method comprising:
   obtaining cardiac computed tomography angiography ("CCTA") scan data comprising a plurality of attenuation values, the CCTA scan data imaging a pool of blood, and a coronary artery having a lumen defined by an artery wall at least partially surrounded by epicardial fat;
   receiving an identification of a first portion of the plurality of attenuation values, the first portion being located within the pool of blood;
   receiving identifications of a plurality of points positioned within the lumen of the coronary artery;
   determining a calcified component threshold based at least in part on the first portion of the plurality of attenuation values;
   generating one or more lines from the plurality of points;
   determining a vessel neighborhood based on the one or more lines;
   generating a series of short-axis cross-sections through the coronary artery based on the one or more lines, each of the short-axis cross-sections comprising a point positioned on one of the one or more lines;
   within each of the series of short-axis cross-sections, identifying at least one epicardial fat region within the vessel neighborhood;
   determining an epicardial fat threshold ("EFT") value based on ones of the plurality of attenuation values within the epicardial fat regions identified within each of the series of short-axis cross-sections;
   within each of the series of short-axis cross-sections, classifying portions of the short-axis cross-section having attenuation values below the EFT value as epicardial fat;
   determining a non-calcified component threshold based at least in part on the first portion of the plurality of attenuation values;
   classifying as lumen a connected portion of CCTA scan data adjacent the one or more lines and having attenuation values greater than the non-calcified component threshold and less than the calcified component threshold;
   within each of the series of short-axis cross-sections, detecting an outer boundary of the coronary artery in the short-axis cross-section, and classifying as arterial wall a portion of CCTA scan data positioned between the outer boundary of the coronary artery and the portion classified as lumen;
   determining an artery wall value as a function of the ones of the attenuation values located within the portion of the CCTA scan data classified as arterial wall;
   identifying at least one of a non-calcified component seed element and a calcified component seed element in the portion classified as arterial wall;
   for each non-calcified component seed element identified, classifying as non-calcified components any portions of the CCTA scan data continuous with the non-calcified component seed element and having attenuation values that are greater than the artery wall value and less than the non-calcified component threshold value; and
   for each calcified component seed element identified, classifying as calcified components any portions of the CCTA scan data continuous with the calcified component seed element and having attenuation values that are greater than the calcified component threshold value.

34. The non-transitory computer readable media of claim 33, wherein the method further comprises:
   displaying on a display device at least a portion of the CCTA scan data with an overlay identifying one or more portions of the CCTA scan data classified as calcified components and one or more portions of the CCTA scan data classified as non-calcified components.

35. The non-transitory computer readable media of claim 33, wherein the method further comprises at least one of:
   determining a non-calcified plaque volume for at least one portion of the CCTA scan data classified as non-calcified components, and
   determining a calcified plaque volume for at least one portion of the CCTA scan data classified as calcified components.

36. The non-transitory computer readable media of claim 33, wherein the artery wall value is an average of ones of the attenuation values located within the portion of the CCTA scan data classified as arterial wall.

37. The non-transitory computer readable media of claim 33, wherein detecting the outer boundary of the coronary artery in each of the series of short-axis cross-sections comprises:
  detecting, relative to the point positioned on one of the one or more centerlines, an outermost and maximum radial gradient boundary.

38. The non-transitory computer readable media of claim 33, wherein detecting the outer boundary of the coronary artery in each of the series of short-axis cross-sections comprises:
  detecting, relative to the point positioned on one of the one or more centerlines, an outermost and maximum radial gradient boundary located within portions of the CCTA scan data having attenuation values greater than the EFT value but significantly less than the non-calcified component threshold value.

39. The non-transitory computer readable media of claim 33, wherein the method further comprises:
  within each of the series of short-axis cross-sections, identifying attenuation values within the lumen of the coronary artery, and determining a normal contrast value based on the attenuation values identified as being within the lumen of the coronary artery; and
  determining a lower contrast level based on the first portion of the plurality of attenuation values, wherein the non-calcified component threshold is determined as a function of the lower contrast level and the normal contrast value of a selected one of the series of short-axis cross-sections.

40. The non-transitory computer readable media of claim 39, wherein within each of the series of short-axis cross-sections, determining the normal contrast value further comprises:
  determining a minimum attenuation value within the first portion of the plurality of attenuation values;
  growing a region from the point positioned on one of the one or more centerlines to include any portions of the CCTA scan data contiguous with the point and having attenuation values greater than the minimum attenuation value and less than the non-calcified component threshold value; and
  determining the normal contrast value as a function of the attenuation values within the region grown from the point positioned on one of the one or more centerlines.

41. The non-transitory computer readable media of claim 39, wherein the method further comprises:
  determining whether the lumen of the coronary artery is completely occluded;
  if it is determined that the lumen of the coronary artery is completely occluded, selecting a distal one of the series of short-axis cross-sections as the selected one of the series of short-axis cross-sections; and
  if it is determined that the lumen of the coronary artery is not completely occluded, selecting a middle one of the series of short-axis cross-sections as the selected one of the series of short-axis cross-sections.

42. The non-transitory computer readable media of claim 33, wherein the one or more lines are splines.

* * * * *